US00RE35585E

United States Patent [19]

Fernandez-Pol

[11] E Patent Number: Re. 35,585

[45] Reissued Date of Patent: Aug. 12, 1997

[54] DNA VECTOR WITH ISOLATED CDNA GENE ENCODING METALLOPANSTIMULIN

[76] Inventor: Jose A. Fernandez-Pol, 437 Hunters Hill Dr., Chesterfield, Mo. 63017

[21] Appl. No.: 510,039

[22] Filed: Aug. 1, 1995

Related U.S. Patent Documents

Reissue of:

[64] Patent No.: 5,243,041
Issued: Sep. 7, 1993
Appl. No.: 748,510
Filed: Aug. 22, 1991

[51] Int. Cl.[6] ..... C07H 21/04

[52] U.S. Cl. ..... 536/23.5; 536/24.31; 435/252.3; 435/69.1; 435/69.7; 435/348; 435/325

[58] Field of Search ..... 530/300, 323, 530/324, 330, 358, 399, 400; 514/2, 6, 12; 435/69.1, 69.7, 69.4, 70.1, 131, 320.1, 240.2, 252.3; 536/23.5, 24.31

[56] References Cited

PUBLICATIONS

J. Sambrook et al. "Molecular Cloning–a laboratory manual" pp. 1230–1231. Cold Spring Harbor, N.Y. 1989.

*Primary Examiner*—Marianne P. Allen
*Assistant Examiner*—Lorraine M. Spector
*Attorney, Agent, or Firm*—Polster, Lieder, Woodruff & Lucchesi

[57] ABSTRACT

A novel DNA sequence is disclosed which encodes a protein associated with many human cancers. This protein is designated as metallopanstimulin-1 (MPS-1) since (1) it is associated with metal ions, particularly zinc; (2) it has been detected in numerous different types of cells; (3) it is associated with rapid cell proliferation. The MPS-1 mRNA and its encoded protein are expressed in normal cells to a much lesser degree than in premalignant or malignant tumor cells, and they are present at very low levels in senescent cells compared to young healthy cells. The DNA sequence and the protein can be used in diagnostic methods such as detection of malignant cells associated with several types of tumors. Thus, this invention discloses a method for determining the presence of certain types of malignant conditions in patients. The MPS-1 cDNA sequence has been inserted into convenient vectors, and a culture of E. coli cells containing the sequence has been deposited with the American Type Culture Collection (ATCC), under accession number ATCC 68656.

20 Claims, 11 Drawing Sheets

DNA Translation
MPS-1 cDNA

| | | | | | | | | | | | | | | | | | | |
|---|---|---|---|---|---|---|---|---|---|---|---|---|---|---|---|---|---|---|
| | | | 29 | | | 38 | | | 47 | | | 56 | | | 65 | | | 74 |
| 5' | ATG | CCT | CTC | GCA | AAG | GAT | CTC | CTT | CAT | CCC | TCT | CCA | GAA | GAG | GAG | AAG | AGG | AAA |
| | Met | Pro | Leu | Ala | Lys | Asp | Leu | Leu | His | Pro | Ser | Pro | Glu | Glu | Glu | Lys | Arg | Lys |
| | | | 83 | | | 92 | | | 101 | | | 110 | | | 119 | | | 128 |
| | CAC | AAG | AAG | AAA | CGC | CTG | GTG | CAG | AGC | CCC | AAT | TCC | TAC | TTC | ATG | GAT | GTG | AAA |
| | His | Lys | Lys | Lys | Arg | Leu | Val | Gln | Ser | Pro | Asn | Ser | Tyr | Phe | Met | Asp | Val | Lys |
| | | | 137 | | | 146 | | | 155 | | | 164 | | | 173 | | | 182 |
| | TGC | CCA | GGA | TGC | TAT | AAA | ATC | ACC | ACG | GTC | TTT | AGC | CAT | GCA | CAA | ACG | GTA | GTT |
| | Cys | Pro | Gly | Cys | Tyr | Lys | Ile | Thr | Thr | Val | Phe | Ser | His | Ala | Gln | Thr | Val | Val |
| | | | 191 | | | 200 | | | 209 | | | 218 | | | 227 | | | 236 |
| | TTG | TGT | GTT | GGC | TGC | TCC | ACT | GTC | CTC | TGC | CAG | CCT | ACA | GGA | GGA | AAA | GCA | AGG |
| | Leu | Cys | Val | Gly | Cys | Ser | Thr | Val | Leu | Cys | Gln | Pro | Thr | Gly | Gly | Lys | Ala | Arg |
| | | | 245 | | | 254 | | | 263 | | | 272 | | | | | | |
| | CTT | ACA | GAA | GGA | TGT | TCC | TTC | AGG | AGG | AAG | CAG | CAC | TAA | 3' | | | | |
| | Leu | Thr | Glu | Gly | Cys | Ser | Phe | Arg | Arg | Lys | Gln | His | *** | | | | | |

DNA Translation
MPS-1 cDNA

| | | | | | | | | | | | | | | | | | | |
|---|---|---|---|---|---|---|---|---|---|---|---|---|---|---|---|---|---|---|
| 1 | CG | ACC | TAC | GCA | CAC | GAG | AAC | ATG | CCT | CTC | GCA | AAG | GAT | CTC | CTT | CAT | | 47 |
| 1 | | | | | | | | M | P | L | A | K | D | L | L | H | | 9 |
| 48 | CCC | TCT | CCA | GAA | GAG | GAG | AAG | AGG | AAA | CAC | AAG | AAG | AAA | CGC | CTG | GTG | | 95 |
| 10 | P | S | P | E | E | E | K | R | K | H | K | K | K | R | L | V | | 25 |
| 96 | CAG | AGC | CCC | AAT | TCC | TAC | TTC | ATG | GAT | GTG | AAA | TGC | CCA | GGA | TGC | TAT | | 143 |
| 26 | Q | S | P | N | S | Y | F | M | D | V | K | C | P | G | C | Y | | 41 |
| 144 | AAA | ATC | ACC | ACG | GTC | TTT | AGC | CAT | GCA | CAA | ACG | GTA | GTT | TTG | TGT | GTT | | 191 |
| 42 | K | I | T | T | V | F | S | H | A | Q | T | V | V | L | C | V | | 57 |
| 192 | GGC | TGC | TCC | ACT | GTC | CTC | TGC | CAG | CCT | ACA | GGA | GGA | AAA | GCA | AGG | CTT | | 239 |
| 58 | G | C | S | T | V | L | C | Q | P | T | G | G | K | A | R | L | | 73 |
| 240 | ACA | GAA | GGA | TGT | TCC | TTC | AGG | AGG | AAG | CAG | CAC | TAA | AAG | CAC | TCT | GAG | | 287 |
| 74 | T | E | G | C | S | F | R | R | K | Q | H | | | | | | | 84 |
| 288 | TCA | AGA | TGA | GTG | GGA | AAC | CAT | CTC | AAC | AAA | CAC | ATT | TTG | GAT | | | | 329 |

*Fig. 3.*

DNA Translation
MPS-1 cDNA

| | | | | | | | | | | | | | | | | | |
|---|---|---|---|---|---|---|---|---|---|---|---|---|---|---|---|---|---|
| | | | 29 | | | 38 | | | 47 | | | 56 | | | 65 | | | 74 |
| 5' | ATG | CCT | CTC | GCA | AAG | GAT | CTC | CTT | CAT | CCC | TCT | CCA | GAA | GAG | GAG | AAG | AGG | AAA |
| | Met | Pro | Leu | Ala | Lys | Asp | Leu | Leu | His | Pro | Ser | Pro | Glu | Glu | Glu | Lys | Arg | Lys |
| | | | 83 | | | 92 | | | 101 | | | 110 | | | 119 | | | 128 |
| | CAC | AAG | AAG | AAA | CGC | CTG | GTG | CAG | AGC | CCC | AAT | TCC | TAC | TTC | ATG | GAT | GTG | AAA |
| | His | Lys | Lys | Lys | Arg | Leu | Val | Gln | Ser | Pro | Asn | Ser | Tyr | Phe | Met | Asp | Val | Lys |
| | | | 137 | | | 146 | | | 155 | | | 164 | | | 173 | | | 182 |
| | TGC | CCA | GGA | TGC | TAT | AAA | ATC | ACC | ACG | GTC | TTT | AGC | CAT | GCA | CAA | ACG | GTA | GTT |
| | Cys | Pro | Gly | Cys | Tyr | Lys | Ile | Thr | Thr | Val | Phe | Ser | His | Ala | Gln | Thr | Val | Val |
| | | | 191 | | | 200 | | | 209 | | | 218 | | | 227 | | | 236 |
| | TTG | TGT | GTT | GGC | TGC | TCC | ACT | GTC | CTC | TGC | CAG | CCT | ACA | GGA | GGA | AAA | GCA | AGG |
| | Leu | Cys | Val | Gly | Cys | Ser | Thr | Val | Leu | Cys | Gln | Pro | Thr | Gly | Gly | Lys | Ala | Arg |
| | | | 245 | | | 254 | | | 263 | | | 272 | | | | | | |
| | CTT | ACA | GAA | GGA | TGT | TCC | TTC | AGG | AGG | AAG | CAG | CAC | TAA | 3' | | | | |
| | Leu | Thr | Glu | Gly | Cys | Ser | Phe | Arg | Arg | Lys | Gln | His | *** | | | | | |

*Fig. 4.*

DNA VECTOR WITH ISOLATED CDNA GENE ENCODING METALLOPANSTIMULIN

Matter enclosed in heavy brackets [ ] appears in the original patent but forms no part of this reissue specification; matter printed in italics indicates the additions made by reissue.

The research which lead to this invention was supported by Merit Review Funds No. 001 from the Department of Veterans Affairs. Accordingly, the Federal Government has certain rights in this invention.

BACKGROUND OF THE INVENTION

This invention is in the fields of genetic engineering, molecular biology, and cancer diagnosis and treatment. It relates to a human gene and its encoded mRNA and protein, which have been discovered to be present at abnotmally high quantities in numerous different types of cancers.

Cancer, Growth Factors and Oncogenes

The cancer phenotype consists of several distinct characteristics such as indefinite proliferative life span, anchorage-independent growth, low growth factor requirements, invasion and metastasis; in addition, cancerous cells can synthesize their own growth factors, which leads to cell proliferation that is independent of the otherwise carefully regulated supply of growth factors and growth-related hormones (8,11,12,15,16; full citations to articles cited by number are provided below, before the claims).

As used herein, "growth factors" refers to proteins and peptides that stimulate or promote cell division. Such growth factors are produced by virtually all types of tumors, and their involvement in cancer is discussed in numerous scientific and medical articles (8,11,12).

Growth factor independence and autonomous growth of cancer cells is due to the constitutive expression of growth factors, their membrane receptors, or intracellular signal pathways which ultimately leads to induction of DNA synthesis and cell division. The constitutively expressed growth factors, which function as transforming proteins in the neoplastic cell, may be encoded by oncogenes, or alternatively, their expression may be under the control of oncogenes.

At least 80 different oncogenes have been identified, each encoding a specific protein that is involved in certain specific types of cancer (12,16). For example, the c-myc oncogene and its protein are involved in breast and colon carcinomas, while the c-erbB-2 oncogene and its protein are involved in breast and ovarian carcinomas (12,16).

Many oncogenes enable continuous cell proliferation by either encoding the growth factor protein or inducing the expression of growth factor proteins which are secreted by the cells (12, 16). The secreted proteins can interact with and stimulate growth-mediating receptors on the surfaces of the same cells that secreted the proteins. This self-stimulating property of cancerous cells has been termed "autocrine secretion" (11,12,16).

There are peculiar types of autocrine growth factors, produced by various normal and cancerous cells, which possess both growth stimulatory and inhibitory activities in the same molecule (11,12,13). The growth response to these bifunctional growth factors is largely dependent on cell type and culture conditions (6). For example, transforming growth factor beta-1 (TGFβ-1) a 25,000 dalton disulfide-linked homodimer is mitogenic for many fibroblastic cell lines and growth inhibitory for diverse epithelial cell types including lung carcinoma, breast carcinoma, and prostatic carcinomas (6). One conspicuous attribute of TGFβ is that it affects the expression of series of genes and oncogenes to either negatively or positively control their expression (11, 13)

For additional information regarding cancer, oncogenes, and cancer-related growth factors, see, e.g., Burck, K. B., et el., Oncogenes (Springer-Verlag, New York, 1988); Kahn, P. and Graf, T. (Eds), Oncogenes and Growth Control (Springer-Verlag, New York, 1986); Cooper, G. M., Oncogenes (Jones and Barlett, Boston, 1990); Guroff, G. (Ed.) Oncogenes, Genes, and Growth Factors (John Wiley & Sons, New York, 1987); Piez, K. A., Sporn, M. B. (Eds) "Transforming Growth Factor-βs", Annals of the New York Academy of Sciences 593: 1–375 (1990).

Human carcinomas, sarcomas, leukemias, lymphomas and other malignant tumors are accountable for high mortality rates. Although many of these tumors may respond to chemotherapy and radiation therapy by a reduction in size, a large number of them are incurable by such treatments unless they are detected at an early stage and eradicated promptly. Therefore, there is a prominent need for methods that would make possible an earlier diagnosis of cancer, a better identification of premalignant cells, a better definition of cancer spread, and a more effective therapy.

DNA probes, RNA probes or antibodies which bind to oncogene or cancer-related products may be used for all these purposes. A prerequisite, however, is to find DNA or mRNA sequences and/or antigens that are more strongly expressed in cancers than in normal adult tissues. In view of the heterogeneity of oncogenes and types of cancer, a number of different diagnostic markers are currently used to establish malignancy. This can lead to various problems and limitations. For example, a DNA sequence or antibody being used to detect a certain type of tumor can fail to detect other types of tumors. Therefore, a need exists for a DNA sequence or antibody which has the ability to detect numerous different types of cancer.

A newly discovered type of protein, which is the subject of this invention, is one such cancer-related growth factor. While most oncogenes and growth factors discovered previously are related only to certain types of tumors, the "metallopanstimulin" (MPS) mRNA and protein disclosed herein appear to be present at abnormally high levels in many different types of tumors. It therefore provides several avenues for diagnosing and treating numerous types of cancer.

Wound Healing and Aging

Growth factors also play important roles in the organism's response to damage by accelerating wound healing (13). For example, topical administration of epidermal growth factor (EGF) or Transforming growth factor-alpha (TGFα) accelerates epidermal regeneration of burns and incisions in vivo (14). Other findings indicate that topical application of a selected group of growth factors will be useful in accelerating healing of various types of injuries (13). Thus, the isolation and characterization of new growth regulatory factors are of important practical interest because of the potential use of such factors in clinical wound healing.

In addition, a fundamental characteristic of normal cells is their limited ability to proliferate in culture (17). Invariably, after an initial mitotic period in culture, normal cells from humans and most other species suffer a gradual decline in their ability to proliferate. Eventually, the decline becomes irreversible. This progression towards a lower activity state has been termed "cellular senescence" (17). Cellular senescence has been studied most often in cultures of human fibroblasts (e.g. WI-38 cells) (17). Numerous studies have indicated that cellular senescence in culture reflects aging in vivo (12). More recent studies have suggested that senescent fibroblasts are unable to proliferate, at least in part, because of selective repression of genes involved in transcriptional activity, such as a protooncogene designated as "c-fos" (17).

For additional information regarding the role of growth factors in wound healing and aging, see, e.g., Piez and Sporn 1990, cited above, and Zenser, T. V. and Coe, R. M. (Eds) Cancer and Aging (Springer-Verlag, N.Y., 1989).

The Inventor's in vitro experimental results indicate that senescent human WI-38 fibroblasts express MPS mRNA at lower levels than in their respective early passage cultures. Senescent cells also show striking, irreversible decreases in the expression of MPS; this is manifested by the loss of MPS inducibility by fetal calf serum and other growth factors (e.g. EGF, TGFα) which have been shown to induce MPS mRNA in young human WI-38 fibroblasts. This loss results at least in part from a reduction in the production of the MPS protein. Thus, reduction in MPS production is associated with senescence and may be one of the causative mechanisms of cellular aging. The Inventor's results suggest that it may be possible to restore senescent cells to a replication-competent state by utilization of MPS protein as an anti-aging factor.

Zinc Finger Proteins

In the past several years, a series of discoveries revealed that several proteins contain metal ions, particularly zinc ions ($Zn^{++}$), that play fundamental roles in stabilizing specific protein conformations (26,28). Many of these metalloproteins are involved in nucleic acid binding and in gene regulation (24,25).

Of particular interest for this invention are the "zinc finger" metal ion binding proteins (25,26,28). The primary finding in this field came from the analysis of the sequence of the protein Transcription Factor III (TFIIIA) from Xenopus laevis (28). This sequence contains nine tandem imperfect repeats that have the consensus sequence (Phe,Tyr)—X—Cys—$X_{2,4}$—Cys—$X_3$—Phe—$X_5$—Leu—$X_2$—His—$X_{3,4}$—His—$X_{2-6}$, where X represents a nonconserved amino acid residue from 2 to 6 residues (28,27). This sequence contains two cysteines and two histidines that form a complex with a single metal ion, particularly $Zn^{++}$ (28). This structural domain was termed "zinc finger" (28,25). The zinc finger domains function as the nucleic acid-binding regions of these regulatory molecules which are involved in the control of gene transcription (24,25). Subsequently, zinc finger motifs have been identified in numerous eukaryotic and vital proteins with transcriptional regulatory activity (22,23,26,29). As discussed below, the MPS sequence disclosed herein has a zinc finger motif, and it shows a significant homology to several other transcriptionally active proteins and growth factors.

One object of the subject invention is to disclose and describe a transcriptionally active growth factor protein designated herein as "metallopanstimulin" (MPS), which is expressed in abnormally high concentrations in numerous different types of cancers and which is expressed in abnormally low concentrations in senescent cells.

Another object of this invention is to provide a convenient DNA vector (such as a plasmid) that contains a cDNA gene which encodes one form of an MPS protein, designated herein as MPS-1, so that any desired quantity of the protein can be generated by various types of host cells in vitro, for subsequent purification and use as described herein.

A third object of this invention is to provide methods of generating DNA or RNA probes and antibodies that bind to MPS mRNA and MPS protein, respectively. Such probes and antibodies can be used for purposes such as hybridization and immunodiagnostic analysis of cells that are suspected of being cancerous.

A fourth object of this invention is to provide analogs and derivatives of MPS which have reduced activity compared to endogenous MPS, for use in inhibiting growth of cancer cells and tumors.

These and other objects will become apparent from the following description and examples.

SUMMARY OF THE INVENTION

The present invention is based upon the discovery of a new and heretofore unrecognized type of cellular mRNA sequence and its encoded protein, designated as metallopanstimulin (MPS). One specific form of this protein, which has been produced from a cDNA gene and isolated in pure form, is designated as MPS-1. The MPS-1 protein, which forms a molecular complex with zinc, has growth stimulating activity in various types of mammalian cells. Both the MPS-1 mRNA and the MPS-1 protein are present in abnormally high concentrations in a wide variety of cancer cells, Therefore, they provide a method for detecting and diagnosing malignancy in many types of tumors. Assays using labelled DNA or RNA probes and antibodies that bind to MPS mRNA and MPS protein, respectively, have shown a high ability to distinguish between cancerous and noncancerous cells.

The available data also indicate that analogues and derivatives of MPS-1 (such as an MPS peptide sequence which has formed a molecular complex with cadmium ions instead of zinc) can reduce the growth of cancer cells by competing with the stimulatory activity of endogenous MPS-1 and/or MPS-1 related proteins. This indicates that such inhibitory analogues and derivatives (which are referred to herein as metallostatin growth inhibitors) are likely to be useful in cancer chemotherapy.

A culture of E. coli cells containing the MPS-1 sequence in a pBR322 plasmid designated as pMPS-1/ST1H2 has been deposited with the American Type Culture Collection (ATCC), and has been assigned accession number ATCC 68656.

BRIEF DESCRIPTION OF THE DRAWINGS

FIG. 2 shows the construction and screening of the cDNA library from which the MPS-1 sequence was isolated.

FIG. 3 shows the nucleotide sequence of the 329 bp fragment of plasmid ST1H2-pcDNA-II, containing the exon coding for the 84 amino acids of human MPS-1 and the 5' and 3' flanking regions. The deduced amino acid sequence is shown in one letter code. The translational initiation site ATG starts at nucleotide position 21 and the TAA termination signal begins at nucleotide 273. The underlined amino acid residues in regions 2–17, 41–55, and 67–84 correspond to three synthetic peptides designated A1, A2, and A3, respectively, that were utilized for antibody production. The numbers in each line refer to the nucleotide(upper) and amino acid(lower) positions. The methionine at position 21 constitutes the NH2-terminus. The nucleotide and amino acid sequence shown in FIG. 3 corresponds to the computerized sequence SEQ ID NO:1 submitted as part of this patent application.

FIG. 4 shows the nucleotide sequence and deduced amino acid sequence of the region of ST1H2 cDNA coding for MPS-1. The deduced amino acid sequence is shown in the three letter code. The amino acid sequence for the zinc finger domain of MPS-1 is boxed at the zinc binding regions and underlined on the connecting region. Numbers above each line refer to the nucleotide position. The termination codon (TAA) is indicated by ***.

Lanes 1, 5, 10 and 14 show control (uninfected) Sf9 cells. Lanes 2, 6, 11, and 15 show control cells infection with AcNPV wild type (WT). Lanes 3, 7, 12, and 16 show control cells infected with AcNPV-Del. Lanes 4, 8, 13, and 17 show cells infected with AcNPV-ST1H2. The AcNPV-Del is a virus in which the ST1H2 gene is deleted. The AcNPV-ST1H2 was generated using the expression vector pJVETL-ST1H2/P17 containing a fusion peptide. The arrow heads to the left of lanes 4, 8, and 17 indicate the position of two proteins that were only found in the cells infected with AcNPV-ST1H2/P17. The arrows on the right of lane 9 and 18 indicate the position of a 12.5-kDa size marker in parallel lanes.

Figure 9:
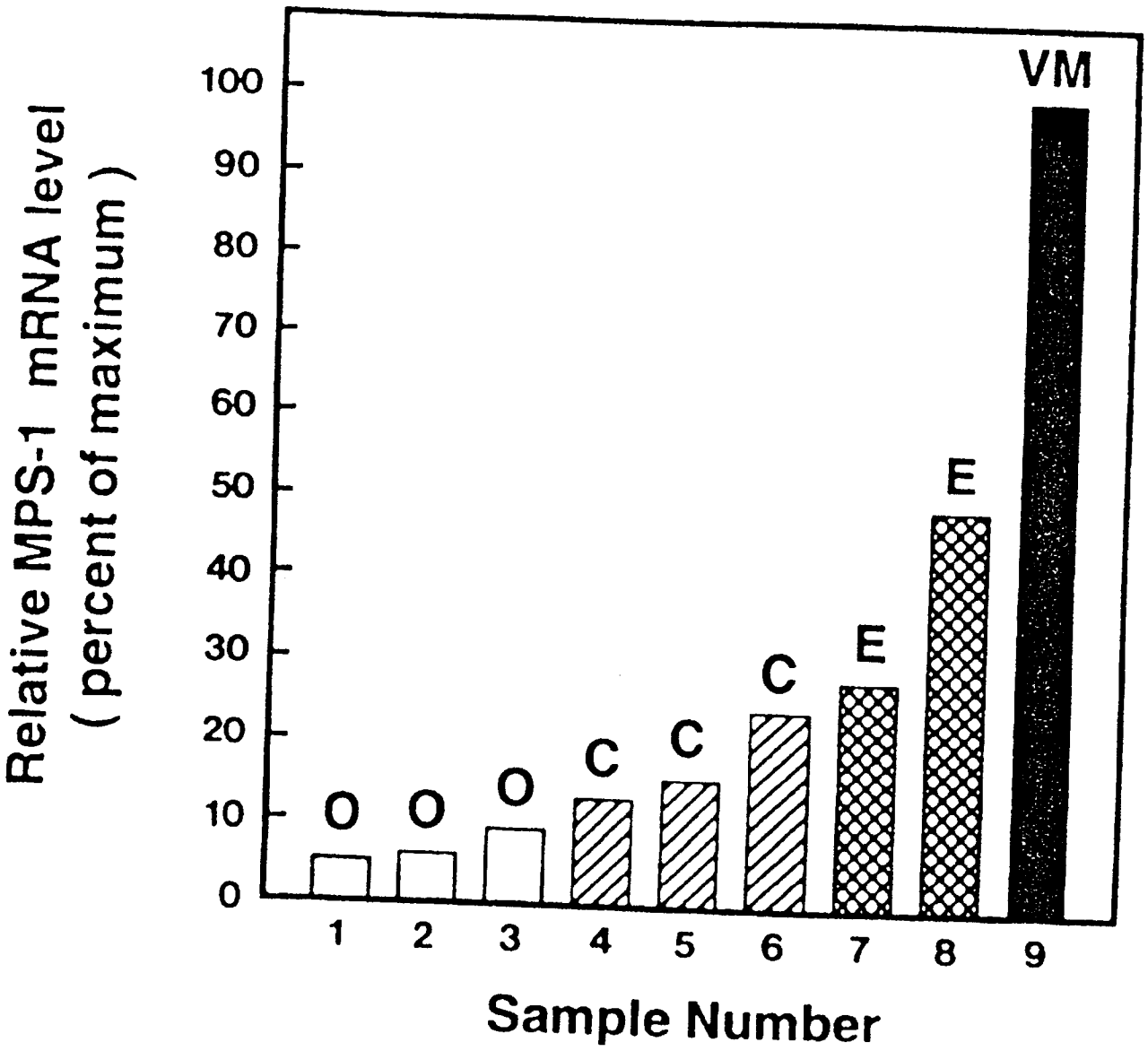

FIG. 9 shows the MPS-1 mRNA level in various human carcinomas (O, ovarian carcinoma; C, carcinoma of the uterine cervix; E, endometrial carcinoma; VM, vulvar melanoma). The widely different levels of MPS-1 mRNA correlate with the pathological degree of malignancy and growth rate of the tumors. Ovarian carcinomas (samples 1–3) and carcinoma of the cervix (samples 4–6) were histologically well differentiated; endometrial carcinomas (samples 7 and 8) were highly invasive to myometrium. Sample number nine (VM) corresponds to a very fast growing malignant melanoma; the patient underwent vulvectomy at the time of sample collection and died 3 weeks later of wide-spread metastatic disease.

DETAILED DESCRIPTION OF THE INVENTION

Figure 1:
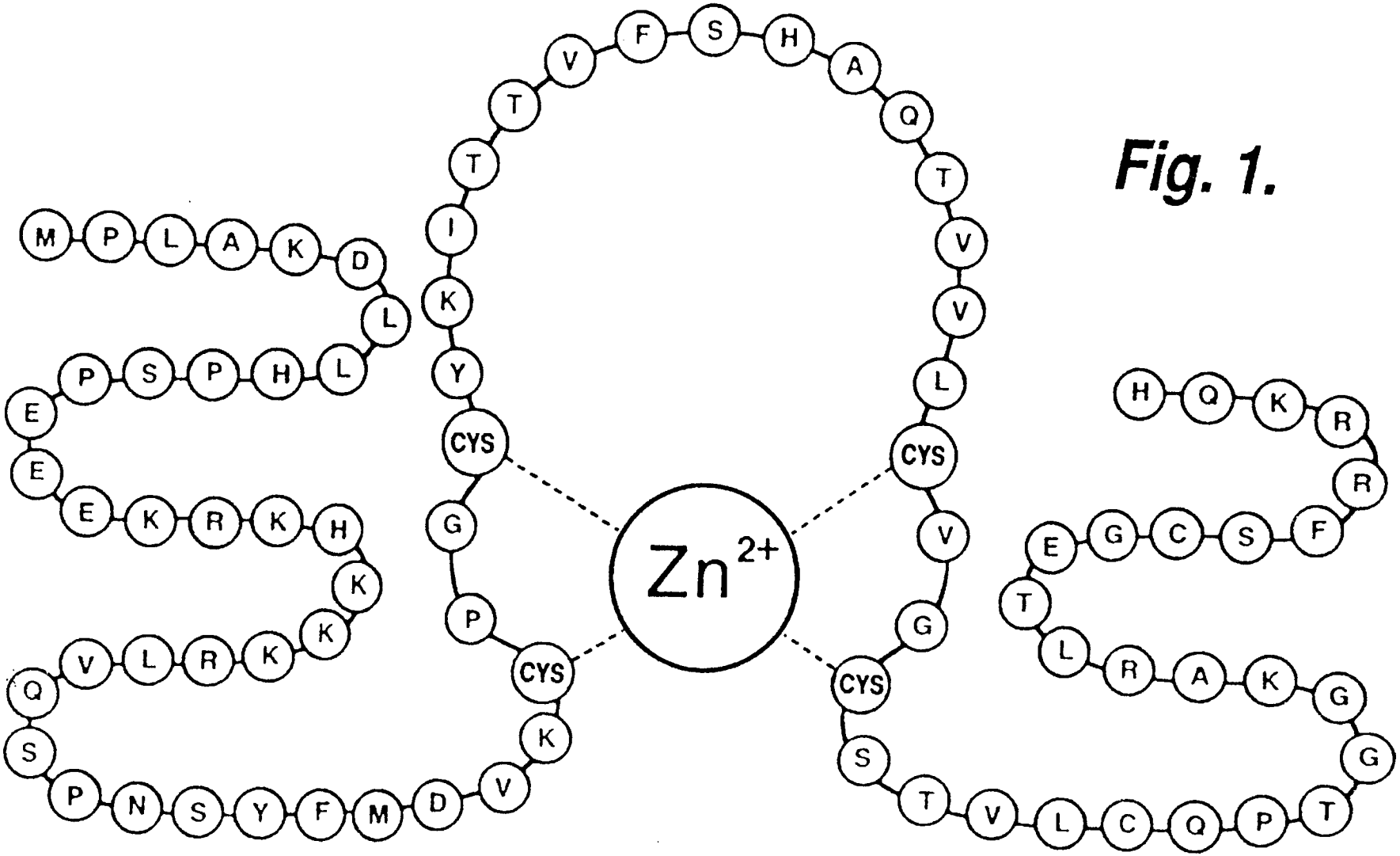
FIG. 1 is a schematic representation of the MPS-1 protein showing the coordination of the zinc atom to cysteine residues.

The present invention relates to a class of newly discovered proteins which have been given the name "metallopanstimulins". One of such protein, which was isolated by genetic engineering techniques from human cells, is designated as MPS-1. The complete amino acid sequence of MPS-1 is disclosed herein, and is shown in FIGS. 1 and 3. The nucleotide sequence of the cDNA MPS-1 gene is shown in FIG. 3.

As used herein, "metallopanstimulin" (MPS) is defined to include synthetic or naturally occurring proteins that have the following properties: (1) they have at least one zinc finger domain; (2) they are amphipathic (sufficiently soluble in both water and lipids to allow them to penetrate lipid membranes while remaining soluble in aqueous fluid); (3) they are secreted from cancerous cells and can act as growth factors on the same cells (autocrine stimulation) and/or other cells(paracrine stimulation) (11); (4) they penetrate into the nucleus where they bind to specific sequences of DNA, referred to herein as MPS response elements; (5) this binding increases the transcription of genes that contain the MPS response elements. Thus, MPS proteins are zinc finger proteins that function as autocrine and/or paracrine growth factors with transcriptional activation effects.

An important characteristic of the MPS-1 gene is that it has been shown to be transcribed into mRNA at abnormally high levels in a wide variety of cancerous cells. In addition, in a number of tumors studied to date, the quantity of MPS-1 mRNA present in the cells is a useful indicator of the aggressiveness and potential lethality of the malignancy. Therefore, the MPS-1 protein offers a method of detecting and diagnosing a broad variety of cancers, as well as a method of assessing the level and aggressiveness of the treatment that will be required to combat the spread of a tumor in a specific patient.

As will be described below, it is possible to create derivatives and variants of naturally occurring MPS which do not have one or more of the characteristics listed above, and which therefore perform certain functions, such as the ability to inhibit rather than stimulate the growth of cancerous cells, or the ability to stimulate the growth of desired cells at higher levels than can be accomplished by endogenous MPS protein. Such altered forms, if they are created and if their relevant characteristics as discussed herein are screened and identified by the methods described below, are referred to as "MPS derivatives".

Preparation of large quantities of the MPS-1 protein enables the preparation of reagents for the assay of MPS-1 and related products in tissues and body fluids for diagnosis of neoplastic and other proliferative diseases. The MPS-1 protein and its analogues, derivatives and fragments may also have utility in the therapeutic treatment of human beings having cancer, showing premature aging, and to accelerate wound healing. In addition MPS-1 may be useful as an additive for cell cultures to stimulate growth.

Creation and Isolation of the MPS-1 cDNA Vector

Isolation of the MPS-1 sequence was performed using the following steps, which are described in more detail in Examples 1 through 3. These steps are shown schematically in FIG. 2. First, MDA468 cells (obtained from the ATCC) from a human breast carcinoma were treated with transforming growth factor beta (TGFβ), a protein which has been shown to activate the transcription of numerous genes (6,7). After a suitable incubation period to allow the effects of the TGFβ activation to be expressed in the messenger RNA (mRNA), the cells were lysed and total cellular RNA was isolated. Poly-adenylated mRNA was isolated by passing the RNA through a cellulose column containing oligodeoxythymidine (oligo-dT) strands affixed to a solid support. The strands with poly-adenosine tails annealed to the immobilized oligo-dT strands and remained in the column, while unwanted RNA passed through. The bound mRNA was then released from the column by increasing the salt concentration, and suspended in solution. It was then treated with various enzymes, as described in Example 1 and as shown in FIG. 2, to generate a variety of bluntended double-stranded (ds) cDNA strands, using the mRNA strands as templates.

The blunt-ended cDNA was then mixed and ligated with oligonucleotide BstX-I linkers having single-stranded 3' overhangs. The mixture was then size-separated by electrophoresis on agarose gels to isolate cDNA's having more than about 500 base pairs (bp); this removed unreacted linkers, as well as very short cDNA's. The selected cDNA's were removed from the gels by elution, and were ligated into a commercially available cloning plasmid (pcDNA-II) which had been opened at a single cleavage site with the BstX-I endonuclease (FIG. 2).

This procedure generated a "library" of approximately 1.6 million different cloning vectors, each vector containing a single cDNA sequence from the MDA 468 cells that had been treated with TGFβ. The vector library was used to transform E. coli cells. The transformed cells were plated onto solid nutrient in Petri dishes, so that clonal colonies could be grown and identified.

Figure 2A:
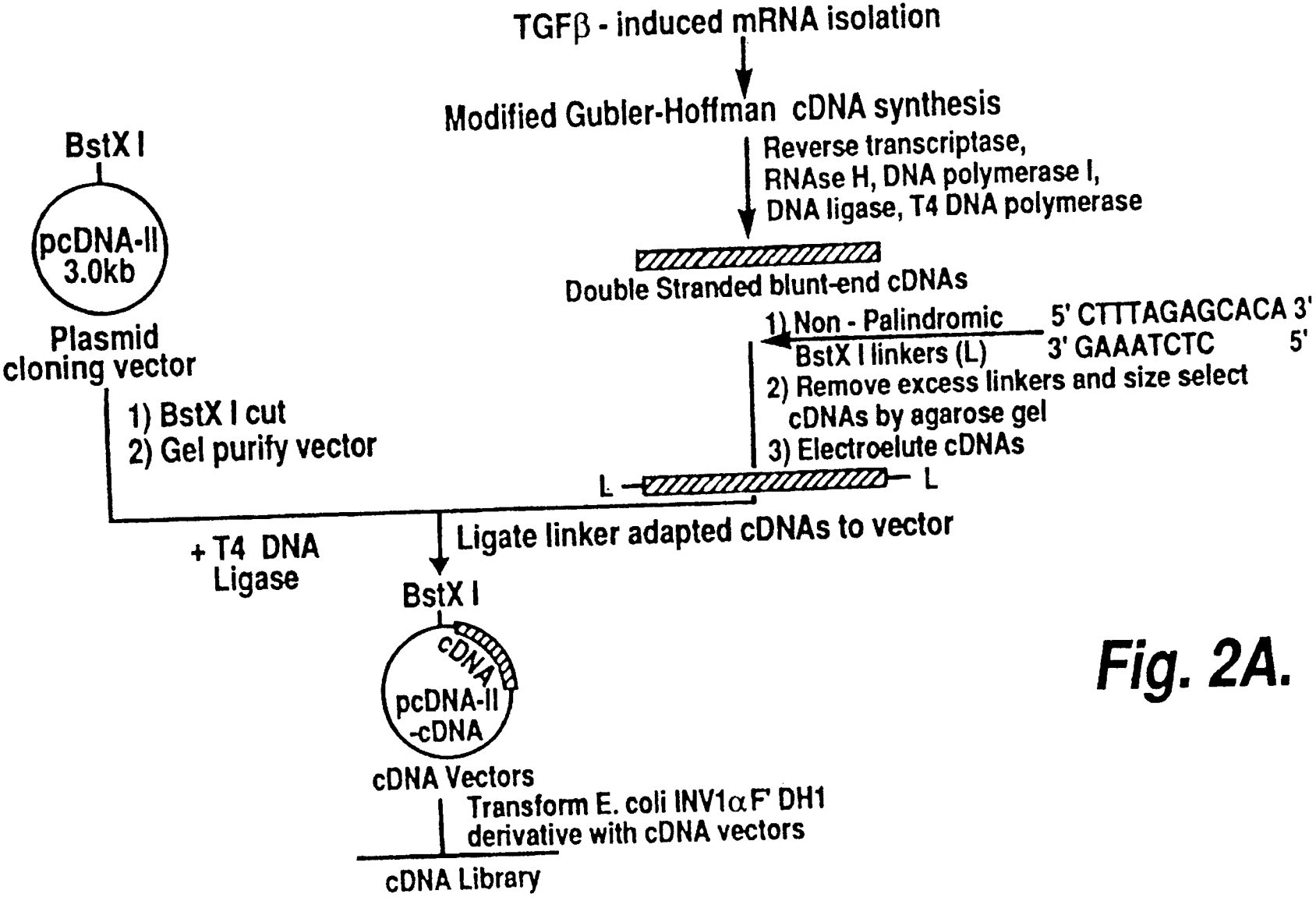
As shown in FIG. 2A, human carcinoma cells were treated with transforming growth factor beta (TGFβ), and their mRNAs were converted into cDNA. The various cDNA's were inserted into cloning plasmids, which were then used to transform E. coli cells to generate a library of numerous different cDNA sequences from which the MPS-1 sequence was isolated by differential hybridization.
Figure 2B:
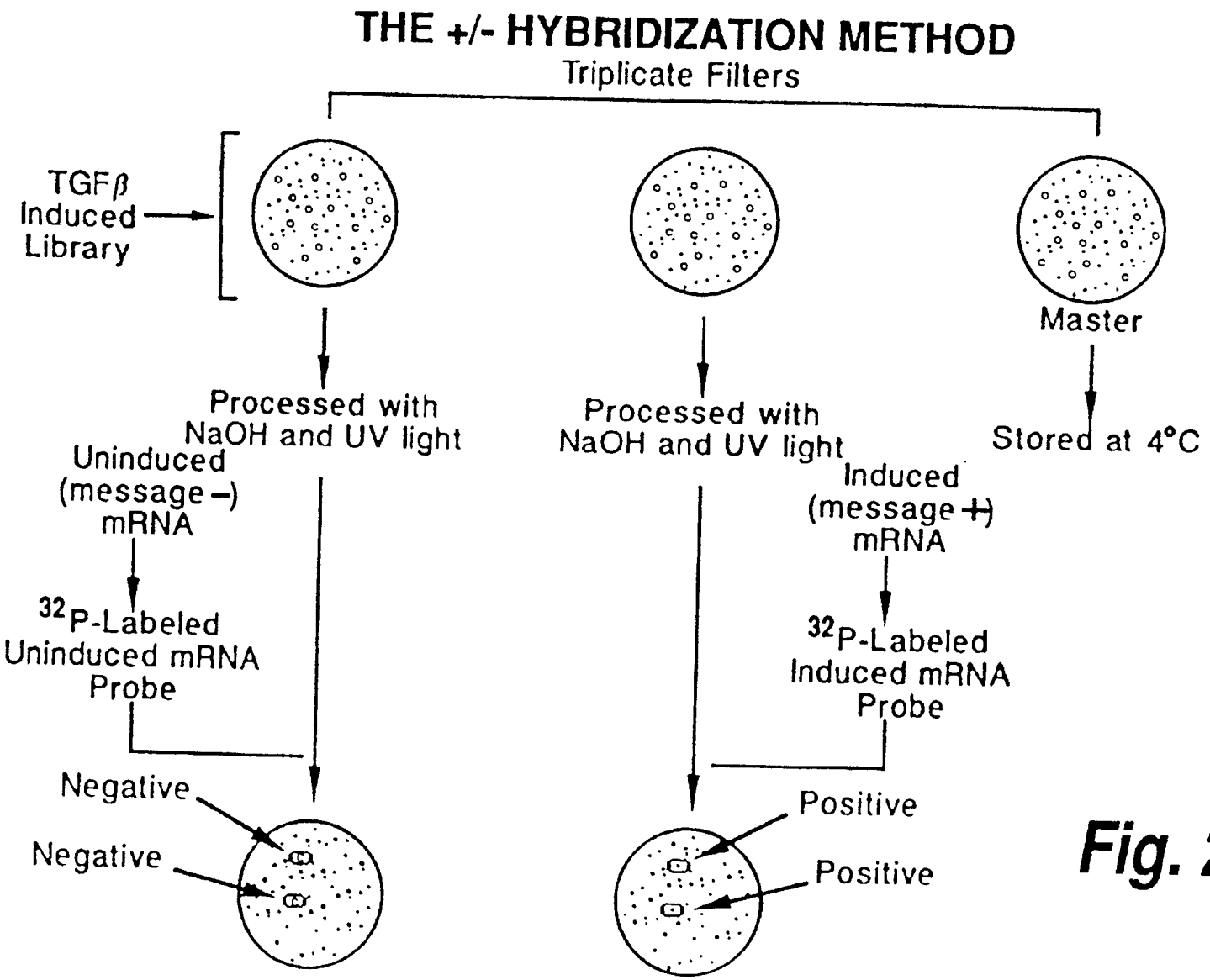
FIG. 2B shows the +/– differential hybridization method. The cDNA library contained in E. coli cells was plated and triplicated using nitrocellulose filters lifts. Two filters were screened using two different sets of mRNA probes; one set (message+) was derived from mRNA from carcinoma cells that had been treated with TGFβ, and one set (message –) was derived from control cells that had not been treated with TGFβ. E. coli colonies containing cDNA which hybridized with the mRNA from treated cells, but which did not hybridize with the mRNA from untreated cells, were identified, isolated, and cloned. Those colonies were further analyzed, and one clonal colony contained a sequence that was later designanted as the MPS-1 cDNA sequence. The third of the triplicate filter lifts was stored as a master to preserve the colonies in the same spatial arrangement as the processed filters.

About 8,000 clonal colonies (0.5% of the total library) of transformed cells containing the cDNA segments were subjected to a screening process, which is described in detail in Example 2 and shown in FIG. 2B. Briefly, two nitrocellulose filters were sequentially pressed against each Petri dish. Each filter picked up cells from the clonal colonies, and the newly established colonies were grown in liquid nutrient to a suitable size. As shown in FIG. 2B this process created two identical filters. This allowed each filter to be screened and compared to its duplicate filter, using two different set of probes. A third identical filter lift was store as a master to preserve the colonies in the same spatial arrangement as the two other filters. The master Petri dishes containing solid nutrient media were also preserved.

Two different sets of probes were used in the screening process (FIG. 2B). Both sets of probes contained mRNA strands from the same line of MDA-468 cells that had been used to generate the cDNA library. The crucial distinction between the two sets of mRNA probes was that one set of probes was isolated from a culture of MDA-468 cells that had been treated with TGFβ; by contrast, the other set of probes was isolated from an untreated culture of cells. Both sets of probes were labelled using a radioactive isotope of phosphorus ($^{32}P$).

When the mRNA probes were ready, they were hybridized with filters which had been treated to break up the E. coli cells and denature the DNA to expose single-stranded DNA. If a radiolabelled mRNA probe was complementary to the cDNA sequence that had been inserted into the cloning plasmid that had entered a particular colony of transformed cells, then the mRNA would bind to the cDNA and remain attached to the filter when the unattached mRNA was washed off.

After the filters were processed in this manner, they were exposed to autoradiographic film, to indicate where radioactive mRNA probes had become affixed to the filters. A dark spot on an autoradiograph indicated that a high concentration of radiolabelled probe had become attached to the filter at that location.

This duplicate screening process allowed the identification of clonal colonies containing cDNA sequences that annealed to mRNA probes from cells treated with TGFβ, but which did not anneal to mRNA probes from untreated cells. This was done by comparing the autoradiographs generated by duplicate filters screened by each set of probes. In the great majority of the clonal colonies, the locations of the dark spots were identical on both corresponding filters, indicating that particular mRNA sequence had not been affected by the TGFβ treatment. However, in a small number of instances (approximately 40 out of 8,000), a dark spot appeared on the plate that had been screened with mRNA from cells treated with TGFβ, while no corresponding dark spot was generated by the probes from the untreated cells. That difference indicated that the cDNA vector which had been inserted into that particular colony of cells contained an mRNA sequence that had been stimulated by TGFβ treatment.

Using that process, approximately forty clonal colonies of potential interest were identified. Their positions were identified using the filters, and viable clonal colonies were obtained from the nutrient master plates that had been used to generate the filters. The colonies of interest were given arbitrary designations, depending on which filter they happened to be located on and their location on the filter. One specific clonal colony, designated as the ST1H2 colony because of its position on a specific plate, was analyzed in detail because it contained a cDNA sequence of interest. That cDNA sequence was later designated as the MPS-1 sequence, but that did not occur until after the characteristics of the protein it encoded became clear.

Analysis of the ST1H2 Clone, Which Contained the MPS-1 Sequence

To begin the process of evaluating whether and how the ST1H2 gene was involved in cell growth regulation, experiments were done with cultured cells. Radiolabelled DNA, which was synthesized based on the sequence shown in FIG. 3, was used to hybridize with cellular mRNA from a variety of normal and cancerous cell types, using Northern blot techniques. That work, which is detailed in Example 15, demonstrated that the ST1H2 sequence is present at much higher levels in cancerous cells than in normal cells. For example, the concentration in two standard melanoma cell lines (RPMI-7951 and SK-MEL-28) was approximately ten times higher than in normal WI-38 lung fibroblats.

In concurrent work, the cDNA insert in the ST1H2 plasmid was sequenced by the methods described in Example 1. The nucleotide sequence [of the 5' and 3' nontranslated regions] and the [protein-coding region] amino acid sequence of the protein are printed in FIG. 3 and FIG. 4; these sequences correspond to computerized SEQ ID NO:1. FIG. 3 also shows the 5' and 3' nontranslated regions [amino acid sequence of the protein, using the one-letter amino acid code]. There are 84 amino acid residues, with an unmodified molecular weight of 9,460 Daltons.

Subsequently, the inventor used a computer program (DNASIS, Hitachi, Brisbane, Calif.) to compare the ST1H2 cDNA sequence to other DNA sequences available in computer-readable form on compact disk (Hitachi CD/ROM, version 66, which is generated using databases maintained by the National Institutes of Health (NIH) and the European Molecular Biology Organization (EMBO) (31). A search of those databases revealed that the ST1H2 sequence has a significant degree of homology with several genes that encode transcription activating proteins, including two genes from Xenopus laevis designated as XELZNF5 and TFIIIA, both of which contain regions known as "zinc fingers". A substantial degree of homology with a zinc finger gene from Drosophila melanogaster designated as hunchback was also detected. Moreover, a lesser degree of homology with several other zinc finger proteins was detected during the computerized sequence analysis.

Based on those homologies and on the positioning of two closely-paired cysteine residues at positions 37 and 40 and two more closely-paired cysteine residues at positions 56 and 59 (each pair separated by two amino acid residues), it was recognized that the protein encoded by the ST1H2 sequence was a zinc finger protein as shown in FIG. 1. Four cysteine residues form a tetrahedral complex with a $Zn^{++}$ ion, which provides structural stability to the finger conformation (28). In FIG. 4, the zinc finger domain is underlined in the connecting region and the four cysteine residues that bond to the zinc ion are enclosed in boxes.

To evaluate the existence of hydrophobic and hydrophilic regions in the ST1H2-encoded protein, a protein analysis software system (Prosis, Hitachi) was used. This software uses the method of Kyte and Doolittle (21) which assigns a hydrophobic, hydrophilic, or neutral value to each amino acid residue, then it uses a "window" of six residues at a time to calculate a net value which changes as a function of the residue position along the length of the peptide chain. By assessing several residues within a window rather than focusing on individual residues, a better assessment of the behavior of the overall protein can be obtained.

Figure 5:
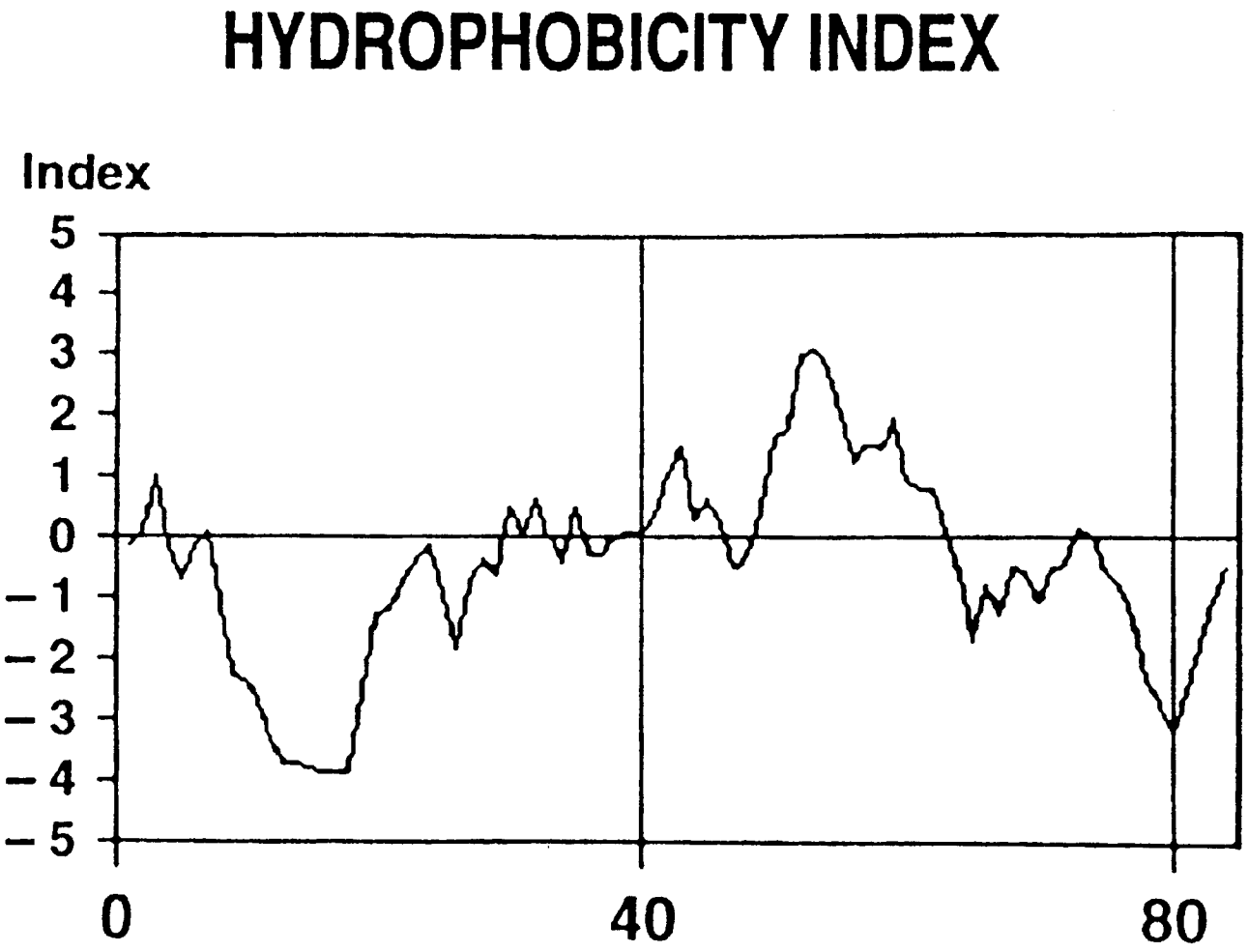
FIG. 5 indicates the hydropathy profile of the MPS-1 84-kD protein. The horizontal axis represents amino acid residue number. A positive value on the vertical axis indicates that the corresponding residue is hydrophobic; a negative value indicates hydrophilicity. The residue window size used was six; the curve was generated by DNASIS (Hitachi).

The result of that analysis is shown in FIG. 5, wherein the horizontal scale indicates the amino acid position in the peptide chain. A positive value on the vertical axis indicates a hydrophobic region, while a negative value indicates a hydrophilic region. The detailed numerical data generated by the analysis indicated that a strongly hydrophilic region near the N-terminus began at residue 7 and ended at residue 24. A hydrophobic region extended from residue 40 to residue 65. Furthermore, the C-terminal region is strongly hydrophilic around position 80. From these results it became clear that the protein encoded by the ST1H2 cDNA was amphipathic; it has at least one strongly hydrophilic region and at least one strongly hydrophobic region.

Transformation of Eukaryotic Cells with the ST1H2 cDNA Sequence containing MPS-1

This invention provides replicable DNA expression vectors possessing DNA encoding the MPS-1 sequence and derivatives in expressible form. When expressed, these vectors can provide any desired quantities of such MPS-1 species. This DNA is novel because the cDNA was synthesized by reverse transcription of mRNA from MPS-1 producing human cells and contains no introns or flanking regions encoding other proteins. Such DNA can be used to transform various procaryote or eukaryote cells. For this purpose, the DNA which encodes the MPS-1 protein or derivatives is ligated into an appropriate vector, the vector containing the MPS-1 sequence is used to transform host cells, the cells are cultured, and the MPS-1 protein produced is purified from the culture media, cells or both. The proteins are purified after the MPS-1 species have accumulated in the culture media or in the nucleus of the eukaryote cells. It is purified using conventional protein purification methods. Optionally, addition of a zinc salt which releases zinc ions will follow the final step to produce properly folded proteins.

In the examples described in this invention, Spodoptera frugiperda (Sf9) insect cell host culture was employed as host cell culture to express the gene of interest (MPS-1) cloned in a Baculovirus transfer vector (18). This system of insect cells was chosen because of its ability to synthesize large amounts of foreign protein if the foreign coding sequence is placed under the control of a strong viral promoter. However, other eukaryotic and prokaryotic cells are suitable for the production of the sequence and protein of the invention as well. Furthermore, synthetic peptides with biological or antigenic activity corresponding to portions of the MPS-1 sequence can be generated by chemical synthesis as described elsewhere in this disclosure.

In this work, which is described in more detail in Examples 5 through 7, a commercially available baculovirus vector and Spodoptera frugiperda (strain Sf9) insect cells were used (18). The specific baculovirus is an Autographa californica nuclear polyhedrosis virus (AcNPV), described in U.S. Pat. No. 4,745,051 (Smith and Summers) and in item 18 listed in the references. The baculovirus vector, a double-stranded circular DNA containing 14 kilobases (kb), is designated as pJVETL, or by the trademark "pBlueBac".

Figure 6:
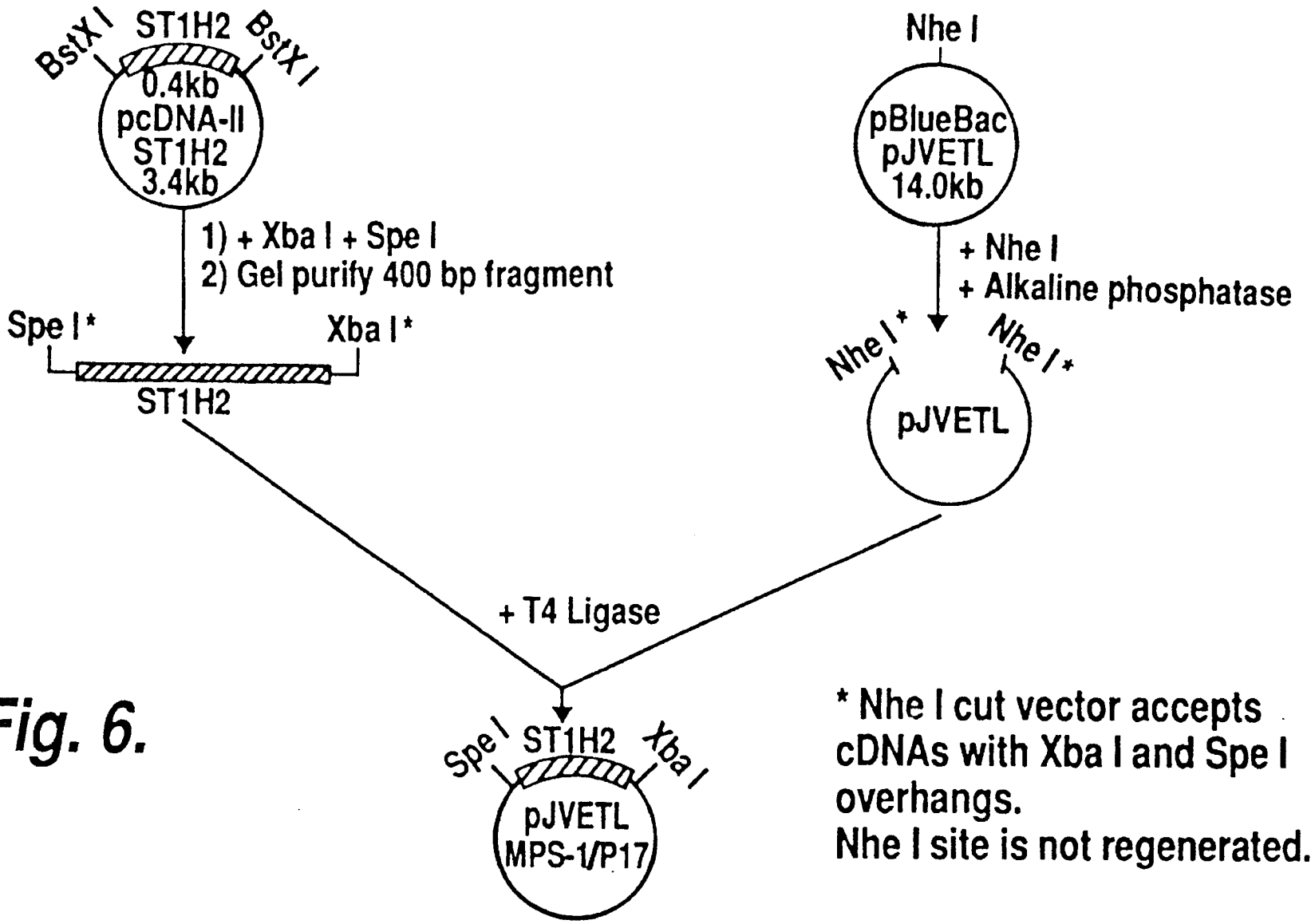
FIG. 6 shows the cloning of the human MPS-1 (ST1H2) sequence into the baculovirus transfer vector pJVETL to construct the recombinant expression vector pJVETL-ST1H2/P17 which expressed two proteins: (1) the endogenous form of MPS-1, and (2) an additional protein which contained seventeen additional amino acid residues at the NH2 terminus.

To insert the cDNA sequence into the viral vector, the cloned ST1H2 E. coli cells were cultured, lysed, and treated to purify the pcDNA-II-ST1H2 plasmid. The plasmid was digested using the endonucleases XbaI and SpeI, and the resulting mixture was size fractionated using gel electrophoresis (FIG. 6). A segment having roughly 400 bp was isolated and eluted from the gel, and was ligated into the pJVETL baculovirus DNA, which had been digested with NheI (an endonuclease that generates overhangs that are compatible with XbaI and SpeI overhangs). After ligation with T4 ligase, a plasmid that was designated as the pJVETL/MPS-1/P17 was generated (FIG. 6).

Figure 7:
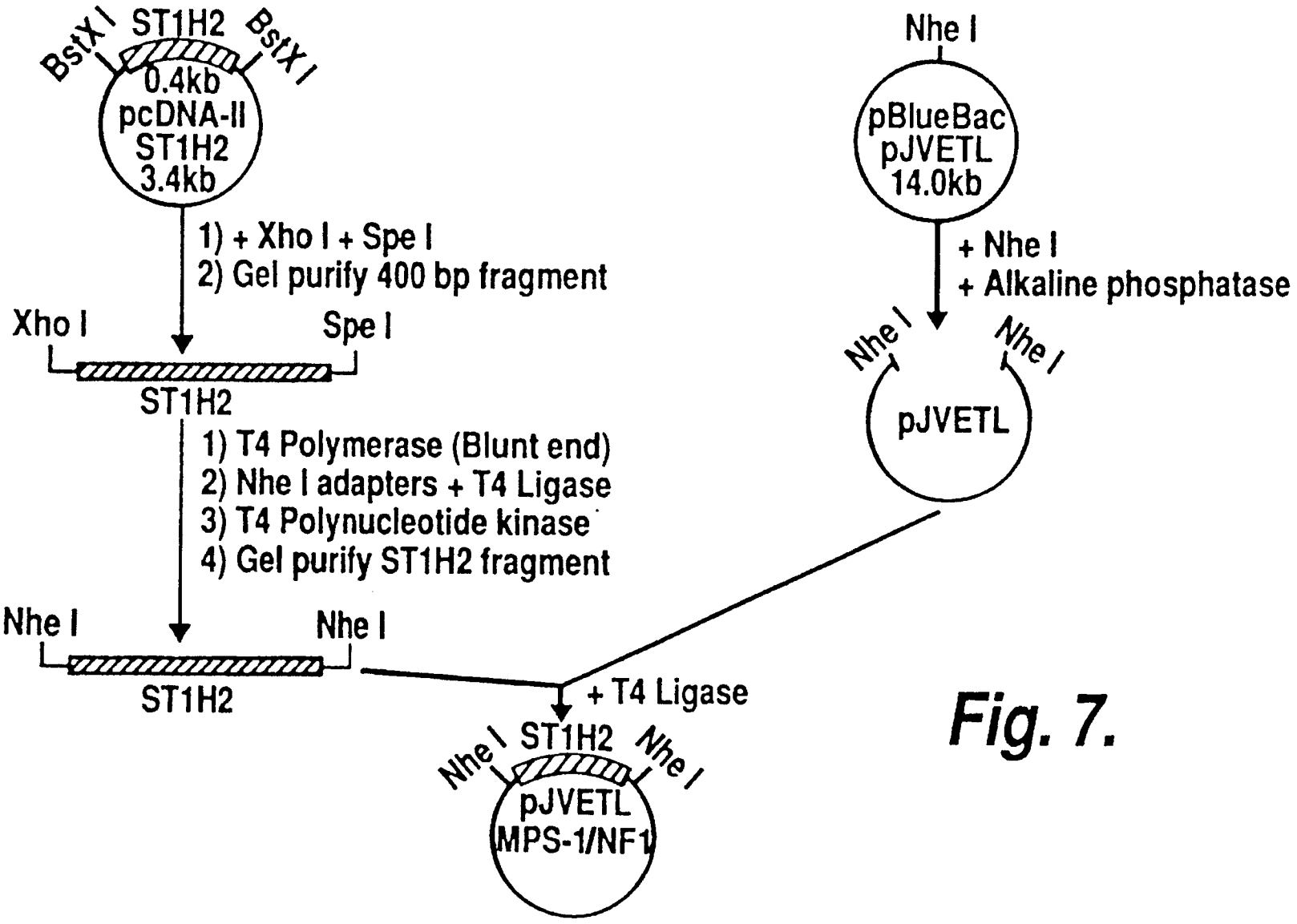
FIG. 7 shows the cloning of the human MPS-1 (ST1H2) sequence into the baculovirus transfer vector pJVETL to construct the recombinant expression vector pJVETL-ST1H2/NF1 which expressed the endogenous form of MPS-1.

The reference to "P17" in the plasmid name indicates that this plasmid generates two different forms of MPS-1: (1) the endogenous form, and (2) a larger variant that contains an additional 17 amino acids at the N-terminus, due to a start codon spuriously located in one of the oligonucleotide linkers used for the library construction, which is in the same reading frame as the natural MPS-1 start codon (Table 1). Both proteins show up as closely-spaced bands in lanes 4, 8, and 17 in FIG. 8. Additional work, which is described in detail in Example 2, and is schematized in FIG. 7 and Table 2, led to the elimination of the interposed start codon and the construction of the recombinant expression vector pJVETL-MPS-1/NF-1 which produces only the natural non-fusion (NF) MPS-1 protein species.

TABLE 1

CLONING OF THE ST1H2 SEQUENCE INTO pJVETL TO CONSTRUCT THE RECOMBINANT EXPRESSION VECTOR pJVETL-ST1H2/P17 CONTAINING A FUSION PEPTIDE

```
Polyhedrin Gene   5' . . . TAATAAAAAAAACCTATAAAT 3'
pcDNA II
linker              Xba I                                   Bst XI
                  5' CTAG ATG C ATG CTC GAG CGG CCG CCA GTG TGC
                  TCT AAA G
ST1H2             CG ACC TAG GCA CAC GAG AAC ATG . . . . . . . . . . . .
                  1                          21
                  . . . GAT AAAAAAAAAA
                        329
pcDNA II
linker                                       Spe I
                  CTTTAGAGCACACTGGCGGCCGTTA . . . 3'
```

Nucleotide sequences of the wild-type polyhedrin gene and pcDNA II linker surrounding the site of recombination and the initiation codons ar shown. The numbering system is based upon the initiation codon of the ST1H2 sequence being designated 21. The in frame initiation codons are underlined.

TABLE 2

CLONING OF THE ST1H2 SEQUENCE INTO pJVETL TO CONSTRUCT THE RECOMBINANT EXPRESSION VECTOR pJVETL-ST1H2/NF1 FOR NON-FUSION PROTEIN

```
Polyhedrin Gene 5' . . . TAATAAAAAAAACCTATAAAT 3'
Nhe I adaptor + Nhe I
pcDNA II
linker              adaptor      Xho I                    BstX I
                  5' CTAGCCCGGGTCGAGCGGCCGCCAGTGTGCTCTAAAG
ST1H2               CG ACC TAG GCA CAC GAG AAC ATG . . . . . . . . . . . .
                    1                          21
                  . . . GAT AAAAAAAAAA
                        329
pcDNA II
linker +                                     Spe I
                  5' CTTTAGAGCACACTGGCGGCCGTTACTAGGCCGGG 3'
Nhe I adaptor
```

Nucleotide sequences of the wild-type polyhedrin gene and pcDNA II linker surrounding the site of recombination and the initiation codons are shown. The numbering system is based upon the initiation codon of the ST1H2 sequence being designated 21.

To evaluate the fate and localization of the MPS-1 protein, insect cells were infected with recombinant viruses containing the MPS-1 sequence. After radioactive labelling, culture media, cytoplasmic and nuclear extracts were separated and analyzed by electrophoresis and autoradiography. This work is described in more detail in Example 8. As shown in lane 8 of FIG. 8, a substantial amount of the MPS-1 and MPS-1/P17 protein species are secreted by the cells. In addition, the great majority of these proteins inside the cell were transported into the nucleus as indicated by comparison of lanes 13 and 17. Thus, as predicted by computer analyses and subsequently confirmed in the laboratory, the MPS-1 is a protein capable of reaching the nucleus. It is also secreted by the cells into the extracellular fluid.

MPS Protein Species and Analogs

This invention relates to a newly discovered type of protein, which has been named "metallopanstimulin" (MPS) by the Inventor in view of three relevant characteristics. First, it is a metalloprotein, a polypeptide that forms a complex with metal ions such as zinc. Second, it has growth-stimulating activity in mammalian cells. And third, as suggested by the Greek root word "pan," which means "all," it has been shown to exist in many different cell types, including non-cancerous cells as well as numerous different types of tumor cells.

This newly discovered class of metalloprotein is exemplified by an MPS species designated herein as "MPS-1." As used herein, the term "MPS-1," when used by itself, refers to the complex that is formed when the MPS-1 polypeptide incorporates a zinc ion and creates a zinc finger structure, as shown in FIG. 1. The term "MPS-1 polypeptide" refers to the polypeptide alone, without the zinc ion.

Variants of MPS-1 from both human and non-human mammalian species (such as bovine, equine, porcine, or murine species) are also included within the definition of metallopanstimulin, if they show substantial homology with the MPS-1 polypeptide sequence and if they show biological activity as described below.

This invention also relates to analogs of the MPS-1 complex and the MPS-1 polypeptide. An "MPS-1 analog" is defined as a polypeptide which (1) has substantial homology with the MPS-1 amino acid sequence set forth in FIG. 3; (2) forms at least one zinc finger domain when mixed with a source of zinc ions; (3) has a transcriptional regulatory function, as described below; and (4) was not identified and characterized prior to the Inventor's disclosure of the existence and sequence of the MPS-1 protein.

As used herein, "substantial homology with the MPS-1 amino acid sequence" refers to a polypeptide in which at least 35% of the residues in a given sequence are identical to corresponding residues in the MPS-1 protein, or at least 35% of the residues have functional correspondence with residues in the analogous MPS-1 domain. As used herein, "functional correspondence" refers to amino acid residues that have the same type of side chains such as basic, hydrophobic, neutral or acid, or the presence of a steric nucleus. In general, a polypeptide defined as MPS-1 species will possess sections considerably homologous with the MPS-1 protein (FIG. 3) or fragments thereof over an uninterrupted domain of at least 30 amino acid residues.

In addition to amino acid sequence homology, an MPS-1 analog must be either an agonist or an antagonist of MPS-1. If it is an agonist, then the analog must display (possibly to a greater or lesser degree) the same biological activity that MPS-1 displays; i.e., it must be capable of stimulating the growth or division of human cells, or the expression of one or more genes which are stimulated by endogenous MPS-1. These characteristics can be measured in vitro. By contrast, if an MPS-1 analog is an antagonist, it must be capable of blocking or inhibiting the stimulatory activity (involving either cell division or expression of one or more specific genes) of MPS-1, in human cells.

Since the MPS-1 protein was discovered to exist in large quantities inside the nucleus while relatively little of the protein was found in the cytosol, and since the zinc finger domains of other transcriptional activator proteins are believed to function by binding directly to certain DNA sequences, it is presumed and believed that MPS-1 stimulates cell division and/or gene expression primarily by permeating into the nucleus and interacting directly with the chromosomes to stimulate or repress the transcription of one or more target sequences. It is also presumed that an MPS-1 analog, in order to have that type of functionality, should also be able to permeate into the nucleus, either because it is amphipathic, or because it may contain a "nucleus localization sequence" (NLS) that helps transport the protein into the nucleus (additional discussion of NLS sequences and fusion peptides is provided below). The ability of a candidate MPS-1 analog to enter the nucleus can be determined by transforming mammalian cells with genes encoding the candidate analog, culturing the cells, isolating the nuclear proteins, and testing the nuclear proteins for the presence of the candidate analog, using methods such as described in Example 8. However, it is also recognized by the Inventor that MPS-1 is secreted by cells into the extracellular fluid; accordingly, the activity of MPS-1 in stimulating cell division might be mediated or enhanced by MPS binding to one or more receptor molecules on the surfaces of cells. Such receptor binding activity is known to stimulate the division of various types of cancer cells; this process is involved in autocrine and paracrine stimulation, mentioned previously. Accordingly, if it is discovered that the MPS-1 protein or its analogs stimulate cell division or gene expression by interacting with one or more MPS receptors on cell surfaces, or if their activity is enhanced by such a binding reaction, then an MPS-1 analog can satisfy the criteria set forth herein if it has sufficient amino acid homology to allow it to bind to and either stimulate (in the case of agonists) or block (in the case of antagonists) activity at such receptors, regardless of whether the analog is also capable of permeating cellular or nuclear membranes or interacting directly with DNA.

MPS-1 Domains

For convenience in identifying the essential domains of MPS-1, four polypeptide sequences have been designated as (1) complete MPS-1, which includes all of the residues (1 through 84); (2) the N-terminal domain, which includes residues 1 (methionine, M) through 36 (lysine, K); (3) the zinc finger domain, which includes residues 37 (cysteine, C) through 59 (another cysteine); and (4) the C-terminal domain, residues 60 (serine, S) through 84 (histidine, H). These domains become apparent upon considering FIG. 1. The zinc finger domain, in the middle, includes the four cysteine residues that complex with the zinc ion. The N-terminal domain is everything to the left of the zinc finger domain, while the C-terminal domain is everything to the right of the zinc finger domain.

The degree of amino acid sequence homology together with the regions responsible for biological activity will determine which polypeptide falls within the definition of MPS-1 species. Functions which are critical for establishing the identity of a polypeptide as of the MPS-1 species are: (a) for inducing morphological changes and growth effects in target cells; (b) for immunological cross-reactivity with antisera produced against recombinant or non-recombinant MPS-1 protein species; (c) for penetrating the nucleus; (d) for specific DNA binding to MPS-1 response elements.

An important factor in determining the identity of a protein as of the MPS-1 species is the ability of anti-MPS-1 antisera to bind to a specific domain of the protein in question. However, it should be recognized that immunological identity and identity related to biological activity, as is the case with other proteins, is not necessarily coexistent. Therefore, a given protein might not bind a given anti-MPS-1 antibody, but it would still fall within the definition of MPS-1 species in terms of its meaningful amino acid homology with MPS-1 and characteristic biological properties.

MPS Conjugates and Chemically-Treated Derivatives

MPS conjugates can be created by covalently bonding MPS or its analogs to other molecules. For example, MPS-1 can be covalently linked to a solid support, such as various types of glass, plastic, or Sepharose beads, using chemical techniques that are well known to those skilled in the art. The immobilized MPS-1 can then be used in immunoassay techniques, or for the purification of DNA fragments which bind to MPS-1, anti-MPS-1 antibodies, and possibly receptor molecules which interact with MPS, if such receptors exist.

For diagnostic procedures, such as determining the levels of MPS-1 in biological fluids using competitive immunoassays, MPS-1 or its analogs can be radioactively labelled using any of several isotopes. For example, the MPS-1 protein can be radioiodinated by the chloramine T procedure which couples labelled iodine to the protein. Alternately, by adding a radiolabelled amino acid to the cell culture medium while the MPS protein is being expressed by genetically transformed cells, the radiolabel can be incorporated into the MPS protein itself. As another option, MPS-1 and its analogs can be coupled, either directly or indirectly, to fluorescent molecules such as fluorescein or phycoerythrin, or to enzymes that are detected by means of chromogenic reactions, such as alkaline phosphatase; such methods will enable the use of fluorescent or ELISA (enzyme-linked immunosorbent) assays.

A covalent linkage which will couple MPS-1 or an MPS analog to a solid support, labelling molecule, or other molecule can be created using chemical derivatization of any of numerous reactive groups which are present in the MPS-1 amino acid chain or at the N-or C-termini, using means that are well known in the art (51). For example, MPS-1 can be derivatized in a manner that will allow it to be conjugated to other molecules by using any of the following groups: (1) N-acyl derivatives of the amino terminal amino acid or of a residue containing an amino moiety, such as lysine 5 (the lysine residue at position 5) or arginine 17; (2) O-acyl derivatives of residues containing hydroxyl moieties, such as serine 11, serine 27, serine 30, or serine 78; (3) aliphatic esters or amides of the carboxyl terminus or residues containing carboxyl moieties, such as aspartate 6 or aspartate 34.

In some situations (for example, if the MPS conjugate will be used in an affinity column to purify polyclonal antibodies that bind to various domains of MPS-1), it is likely to make little or no difference which residue is derivatized for crosslinking purpose. However, if the MPS portion of the conjugate needs to remain biologically active, then it is presumed that the zinc finger must not be directly altered or sterically hindered by the conjugation process. In such situations, it will be necessary to use conjugates in which the amino acid residue that is crosslinked should not be in or closely adjacent to the zinc finger. If that requirement applies, it can be accomplished by any of several means. The derivatization reaction can be controlled to limit the number of residues per polypeptide that are derivatized, so that only a limited fraction of a certain type of residue will be derivatized. Subsequently, a purification procedure can be used to isolate polypeptides that have been derivatized in a manner that did not alter or affect the zinc finger domain. This can be done, for example, by using an affinity column containing monoclonal antibodies that will bind only to unaltered zinc finger regions of the polypeptide. Such techniques for creating biologically active conjugates are within the skill of chemists and biochemists who specialize in protein immobilization.

The crosslinking molecules used to create MPS conjugates may be heterobifunctional. One end of the crosslinking molecule, which has a first type of reactive moiety, can react with a protein having a desired characteristic, while the other end of the crosslinker has a different type of reactive moiety that will react with specific groups of the MPS-1 protein. One such heterobifunctional crosslinking agent is sulfosuccinimidyl 4-(N-maleimidomethyl) cyclohexane-1-carboxylate (Sulfo-SMCC) which can be used to generate derivatives of MPS-1 that are useful for generating antibodies against MPS-1. For example, the MPS-1 protein or a portion thereof can be crosslinked to an immunogenic protein such as keyhole limpet hemocyanin (KLH) by using Sulfo-SMCC. The MPS-1-KLH conjugate increases the efficiency of anti-MPS-1 antibody production after the conjugate containing the MPS-1 polypeptide is injected into laboratory animals such as rabbits as described in Example 10.

Additionally, the molecule used to crosslink MPS to a carrier molecule can be structured so that it will release the MPS from the conjugate after the conjugate enters a cell. One such acid-labile "spacer" molecule which is spontaneously hydrolyzed by acidic conditions inside cells is described in U.S. Pat. No. 4,631,190 (Ryser and Shen 1986).

MPS Fusion Peptides

This invention also relates to "fusion peptides" that contain all or a substantial portion of the MPS-1 sequence (or a homologous analog of MPS-1) coupled to an additional polypeptide which has one or more desired functions. For example, certain sequences which are usually present at the amino termini of secreted proteins are known to increase the rate at which polypeptides are secreted by cells; see, e.g., references 19 and 52. As a second example, "nuclear localization sequences (NLS)", mentioned above, are involved in the transport of polypeptides into the nucleus; see, e.g. references 20,52,53,54. A third example involves sequences that are cleaved from polypeptides inside the cytoplasm, to generate "mature" peptides that do not have a methionine residue at the amino terminus; see, e.g., reference 52. If desired, a chimeric gene can be created which will express an MPS peptide sequence coupled to any of those three types of sequences, to provide an MPS fusion peptide having the additional function conferred upon it by the secretion, NLS, or cleavage sequence.

A different class of fusion peptides which has even greater potential importance from the viewpoint of cancer therapy and other types of therapy as well involves MPS sequences coupled to cell-specific carrier sequences. As used herein, cell-specific carrier sequences are polypeptide sequences that can preferentially bind and enter into certain types of cells, without having comparable affinity for other types of cells. For example, many types of cancer cells are known to have certain types of growth factor receptors on their surfaces which are either absent or present at much lower concentrations on the surfaces of normal cells. A number of cancer-related growth factors and their receptors are listed and reviewed in reference 16; these include TGFα receptor (which is present in abnormally high quantities on the surfaces of certain human epidermoid carcinoma cells) and interleukin-2 (which is a growth factor for both T cells and T lymphoma cells). Accordingly, it is possible to couple such ligands to the MPS-1 polypeptide sequence to create a fusion peptide, which can be expressed by a single chimeric gene in genetically transformed cells; see e.g. references 55 and 56. The fusion peptide can be mixed with a source of metal ions other than zinc, such as cadmium or platinum, to generate an MPS analog which may be capable of suppressing rather than stimulating cell division. The carrier sequence will help to recognize and carry the MPS analog into the cancerous target cells expressing the specific type of cell surface receptor. Furthermore, these fusion peptides should make it possible to control MPS-1 mediated gene expression in specific cell types.

Site-Specific Mutated Analogs of MPS-1

An important class of MPS-1 analogs includes analogs having one or more amino acid residues which have been intentionally replaced by other residues in order to enhance the stimulatory activity of the analog in comparison to natural MPS-1, or to provide some other desired benefit. For example, the cysteine 64 and/or cysteine 77 residues, which are not involved in the zinc finger domain of MPS-1, can be replaced by serine or another amino acid residue, which would prevent the mutated analog from forming unwanted disulfide bridges at these sites. Alternately, in the case of MPS antagonists, the purpose of a site-specific mutation may be to enhance the growth-inhibiting activity of the analog. No effort is made herein to predict the effects of any such site-specific mutation on the biological activity of the resulting analog, since molecular biology has not yet reached a level where it is possible to reliably predict which specific amino acid substitutions will lead to greater activity or affinity for a target substrate. Nevertheless, it is possible, using computers and molecular modelling, to identify promising MPS candidate analogs for screening tests. The selected candidate MPS analogs can be generated using the techniques of genetic engineering; this is easily done using M13 viral vectors. The resulting MPS analogs can then be screened to determine whether they do in fact have a desirable increase in growth-stimulating or growth-suppressing activity, using routine screening tests as described herein. If such analogs are derived from the MPS-1 sequence disclosed herein, and if they retain substantial homology with the MPS-1 sequence disclosed herein, and if the screening tests require no more than routine skill in the art, then such MPS-1 analogs are within the scope of the subject invention.

Antibodies That Bind to MPS-1

The present invention also concerns novel antibodies which bind to MPS-1, and which may also bind to other naturally occurring MPS species or synthetic MPS analogs. Such antibodies are useful for various diagnostic methods, as described below.

Since this invention discloses the complete amino acid sequence of MPS-1, it is possible to generate MPS-binding antibodies by using the entire recombinant MPS-1 protein as an antigen, or by using selected portions of the MPS-1 sequence, such as the three peptide fragments that are underlined in FIG. 3, which are described in more detail below.

The use of MPS-1 or a portion thereof as an antigen to generate antibodies, and the creation of hybridoma cells that will generate MPS-binding monoclonal antibodies, can be done using conventional techniques. For example, rabbits or mice may be immunized using the recombinant MPS-1 polypeptide produced in genetically transformed host cells, or using a synthetic peptide fragment. The animals are immunized by subcutaneous injection using conventional adjuvants such as Freund's adjuvant, with booster injections of antigen applied as necessary.

As mentioned above, the MPS-1 polypeptide or peptide fragments therefrom can be conjugated to immunogenic proteins such as keyhole limpet hemocyanin (KLH), to increase the efficiency of the antibody-generating process in animals that are injected with the conjugate.

If polyclonal antibodies are desired, they can be obtained from blood serum which can be centrifuged to remove blood cells. Blood serum containing a specific class of desired antibodies is usually called "antiserum". These techniques are described in reference 46.

If monoclonal antibodies are desired, antibody-producing lymphocytes can be obtained from injected animals (usually from spleen) and fused with compatible immortal cells (usually lymphoma cells from the same species). A mixture of different cells having varying characteristics is obtained from the cell fusion process, and a screening process is then performed to identify and isolate a clonal colony of fused "hybridoma" cells which contain a combination of chromosomes that allow that particular cell line to reproduce immortally while also secreting the desired monoclonal antibodies. These techniques are described in, e.g., G. Schreier et al, Hybridoma Techniques, Cold Spring Harbor Laboratory, 1980 and references 5 and 47.

Diagnostic Uses of MPS-1 Probes and Antibodies

The finding in the Inventor's laboratory that the MPS-1 mRNA and protein are expressed in numerous tumors of various origins at greater levels than in normal tissues, and that the MPS-1 mRNA and protein are expressed at very low levels in aging cells, has important implications in the field of cancer diagnosis and treatment. Thus, this invention provides for the diagnostic use of MPS-1 DNA and/or RNA probes and anti-MPS antibodies in detecting cancer cells that express the mRNA sequence and/or protein.

The term "cancer cells" includes epidermoid carcinoma cells, adenocarcinoma cells, undifferentiated carcinoma cells, sarcomatous cells, and other types of cancer cells. The term "tissue" refers to excised cells, exfoliative cells, body fluids such as blood, plasma, serum, urine, etc., and the like. The term "malignant condition" refers to the presence of dysplastic cells including carcinomas and sarcomas in situ, neoplastic, premalignant, malignant, or tumor cells.

The MPS-1 sequence and the protein that it encodes can be used in various types of in vitro diagnostic methods. For example, single-stranded MPS-1 DNA or RNA sequences can be use in tissue autoradiography (39) in in situ non-isotopic hybridization (40), in Northern (7) or Southern (35) blot analyses, or as primers in analytical techniques using polymerase chain reaction (PCR) (37) or any of several variations of PCR technology, including the transcription-based amplification system, the self-sustained sequence replication system, the Q-beta replicase system, and the ligation or ligase-based amplification systems, all of which are reviewed in [D. Y. Kwoh and D T. J. Kwoh, American Biotechnology Laboratory 8(13): 14–25 (October 1990)]. An example of how a DNA probe with the MPS-1 sequence can be used diagnostically is provided below.

Antibodies that bind to MPS-1 can also be used in various types of diagnostic immunoassays, which can involve immunocytochemistry (33), immunoprecipitation (5), immunoblot analysis (3,4), radioimmunoassay (45), flow cytometry (1), enzyme-immunoassay (44,46) or fluorescence assays (2,5,46).

As described in Examples 12 and 13 and as shown in FIG. 9, the MPS-1 mRNA sequence or the MPS-1 protein have been detected in a variety of different types of cancerous tumors, including carcinomas of the ovary, uterine cervix, endometrium, undifferentiated carcinoma cells, and melanomas. By contrast, the MPS-1 mRNA and protein are present in much lower and occasionally undetectable quantities in normal adult cells. In addition, embryologic studies in mice and rats showed that the MPS-1 sequence is present in greater abundance in cells derived from the ectodermal layer than in those derived from endodermal or mesodermal layers. These results suggest that the MPS-1 sequence may be a ubiquitous marker for ectodermally-derived malignancies. Therefore, the MPS-1 cDNA and polypeptide sequences may provide a useful and widely applicable method of detecting the presence of a cancerous or pre-cancerous condition in a patient suspected of having numerous different types of cancer, regardless of which specific type of cancer is involved.

In addition, the widely different levels of MPS-1 mRNA or protein in various different tumors correlated well with the pathological degree of malignancy and growth rate of those tumors. Therefore, the diagnostic methods disclosed herein can provide very useful and quickly available information on how aggressively a cancerous or pre-cancerous condition in a patient should be treated using chemotherapy, radiation therapy, or surgery.

Use of Genetic Probes for Diagnostic Purposes

This invention discloses the use of genetic probes having sequences complementary to the MPS-1 mRNA sequence, for purposes such as determining whether a tissue or fluid sample from a patient contains cancerous cells. In general, a genetic probe is a short segment of "anti-sense" DNA or RNA. If it comes in contact with other DNA or RNA, it will attach specifically to any segment that has a matching sequence of chemicals, called bases, which are like bridges that link strands of the DNAs or RNAs.

The probe is covalently labeled with a substance that allows the presence and the concentration of the probe to be measured. For example, fluorescent groups, chemoluminescent groups, radioactive isotopes or a biotynilated moiety can be conjugated to the probe strand, using well-known methods (38–43, 49).

Before the probe can be used, a tissue or fluid sample from the patient must be properly prepared. Such a sample may contain excised cells from a cohesive tumor, or cells from body fluids such as blood, plasma, serum, urine, etc. If a cohesive tissue sample is used (for example, if an excised tumor is being analyzed to determine whether it is benign or malignant by in situ hybridization), the tissue may be frozen and then cut into thin sections using a cryostat.

Alternatively, the cells may be lysed, and the resulting cellular lysate can be treated in any desired manner to place the DNA or mRNA in condition to interact with the probe. For example, the mRNA can be immobilized on a solid support such as filter paper. In most tests involving MPS analysis, mRNA will be analyzed, since it provides an indication of how strongly the MPS gene is being expressed into MPS protein by the cells. However, it is also possible to analyze the genomic DNA for the presence and quantity of the MPS gene, by denaturing the double-stranded DNA to convert it to single-stranded form.

The tissue or fluid specimen, after it has been prepared, is contacted with the labelled probe having the MPS-1 anti-sense sequence. This contact is carried out under specific conditions of temperature and salinity, which allow the probe to anneal securely to complementary mRNA sequences while suppressing nonspecific binding of probes to homologous but non-complementary sequences.

After a suitable incubation period to allow for proper annealing, the temperature and/or salinity are changed to disrupt any non-specific binding, and unbound probe molecules are washed away and removed. The concentration of firmly-affixed probe molecules is then quantitatively measured, using the fluorescent, radiolabelled, or other detectable characteristic of the probe.

If a high concentration of the probe is present, this indicates that a high concentration of MPS mRNA was present in the patient's cells, which in turn indicates a cancerous condition in the cells. In addition, the concentration of the bound probes can also provide an indication of the degree of malignancy of the cancerous condition (see Example 13 and FIG. 9).

A somewhat different technique for analyzing MPS-1 mRNA sequences in cell samples is referred to as the message amplification phenotyping (MAPPing) technique (36). In this technique, mRNA is first isolated in an aqueous suspension, reverse transcriptase enzyme is used to generate numerous strands of DNA, using the various mRNA strands as templates. After the DNA has been synthesized, the DNA is subjected to polymerase chain reaction (PCR) technique with selected MPS-1 primers to determine whether the synthesized DNA contains the MPS-1 sequence.

For detection of MPS-1 mRNA by the MAPPing technique, two selected MPS-1 primers with the following 5'–3' sequences were used:

Primer 1: ATG CCT CTC GCA AAG GAT CTC (Nucleotides 21–41 of SEQ. ID No. 1)

Primer 2: AAG GAA CAT CCT TCT GTA AGC (Complementary to nucleotides 236–256 of SEQ. ID. No. 1).

Primer 1 will bind to the 3'–5' strand of the MPS-1 cDNA, at the position which spans nucleotides 21 through 41. Primer 2 will bind to the 5'–3' strand of the MPS-1 cDNA, at the position which spans nucleotides 236 through 256. During a PCR cycling procedure, these primers will generate a "short product" segment of double-stranded DNA having 236 bases on each strand, if the MPS-1 sequence was present in the mRNA sample that was treated and tested. If the MPS-1 sequence was not present, then the primers will remain unreacted, and no such short product will be generated. In addition, if the number of reaction cycles is limited (36), the quantity of short product segments can provide an estimate of the concentration of MPS-1 mRNA molecules in the initial sample from the patient.

The MAPPing technique has been used in the Inventor's laboratory with excellent results. Detection of the MPS-1 sequence was accomplished in many tumors from various origins (e.g. gynecological, skin). In contrast, the mRNA was low in normal tissues.

It is worth noting that the mRNA species for human MPS-1 is of low molecular weight, relatively rare, and thus easy to overlook. However, now that its existence has been recognized and its sequence disclosed, cells can be screened for the MPS-1 mRNA sequence using routine procedures. Additional information on the procedures and techniques for carrying out such tests is available in references 40 through 43.

Use of Anti-MPS-1 Antibodies for Diagnostic Purposes

The invention also includes the diagnostic use, in detecting various carcinomas in humans, of antigen or antigens having the characteristics of the MPS-1 antigen, and antigens which are related but not identical to MPS-1 antigen and which are recognized by the antibodies that recognize MPS-1 antigen.

One method of the invention involves the determination of the presence of a malignant condition in the tissues of a subject by examining tissues from the subject for the presence of the MPS-1 protein. The specimen is contacted with an antibody against MPS-1 protein which recognizes a determinant site on the MPS-1 protein. The specific anti-MPS-1 antibodies are labelled and these labels are capable of producing a detectable signal. The contact is carried out under conditions for binding of the antibody to the malignant cells. After contact, the presence of binding of the antibody to the malignant cells in the specimen is observed. That is, the specimen is examined for immune complexes of the antibody and the antigenic site. This immune complex formation is related to the presence of malignant cells in the specimen. The antibodies are also capable of distinguishing such cells from other cell types which may be present in the specimen.

A particular example, by way of illustration and not limitation, of a method in accordance with the invention is a method for the detection of tumor cells in excised breast, ovary, endometrial, or skin tissue by immunochemical staining as follows. The said method is applied to a specimen which is a section of the tumor obtained after removal of the tumor. The tumor that is excised is treated to obtain sections, which treatment initially involves freezing the tumor or tissue, normally freezing immediately after excision. The frozen layer of tissue is then cut into sections using, for example, a cryostat.

The section of the tumor obtained as described above is contacted with the labeled anti-MPS-1 antibodies of the invention under conditions for binding of the antibody to malignant cells. The amount of antibody used is sufficient to produce detectable binding. After incubation, the section is washed to eliminate non-specific binding of antibody. Then, the label is detected and quantified by visual or automatic techniques. The label is capable of producing a detectable signal and may be a radioactive label, a chromophore such as a fluorescer, an enzyme, or the like. The sections may be covered with mounting fluid on a coverslip and then examined with a light or fluorescence microscope to determine the binding of the antibody to the section. The determination of the binding also may include an identification of the location of such binding within the specimen (e.g. nuclear localization of the MPS-1 protein). The binding is related to the presence of malignant cells in the search.

Examples of techniques in which the anti-MPS-1 antibodies of the invention can be employed are immunofluorescent or immunoperoxidase (33,34) detection of the MPS-1 protein. Another example of a technique in which antibodies anti-MPS-1 can be employed is radioactive- or enzyme-link immunoassays (44,45). These assays may be used for the detection of secretion of MPS-1 protein from cells producing MPS-1 as a growth factor into body fluids, including plasma and serum.

The antibodies against MPS-1 can be potentially employed to image metastatic deposits in human patients with tumors in a manner analogous to that described for various solid tumors in the Nuclear Medicine literature (32). The antibody or fragments (5) thereof can be radiolabelled and administered intravenously to a patient who subsequently is imaged using, for example, a gamma camera, positron emission tomography or the like. Similarly, the anti-sense MPS-1 labelled probe may be useful for external scintigraphic detection of tumors.

STARTING MATERIALS

Cultured Cell Lines and Pathological Specimens —The human cell lines were obtained from the American Type Culture Collection (Rockville, Md.). The pathological tissue specimens used were discarded human tissues obtained at the time of surgery. The research use of these tissues was approved by the Human Studies Subcommittee, VA Medical Center, St. Louis, Mo.

Plasmid DNA—The plasmids used in the cloning procedures (pcDNA—II and pBlueBac pJVETL) were obtained from Invitrogen, San Diego, Calif.

Baculovirus Expression Vector System—The use of the baculovirus system was done in accordance with license from Invitrogen, San Diego, Calif. The baculovirus system is described in U.S. Pat. No. 4,745,051.

Bacterial and Insect Cells—E. coli INVIα F 'DH1 (used to generate the cDNA library) and Sf9 insect cells (used to express the MPS-1 cDNA gene after it had been isolated) were obtained from Invitrogen.

Enzymes—The restriction endonucleases used were as follows: BstX I, Xho I, Spe I, Nhe I, Xba I, and Bam HI. They were used according to the supplier's specifications (New England Biolabs, Beverly, Mass.). The following enzymes were obtained from Promega, Madison, Wis.: calf intestinal alkaline phosphatase(CAP), T4 polynucleotide kinase, and T4 polymerase. T4 DNA ligase and various adaptors were obtained from Invitrogen.

Growth Factors—EGF was purchased from Biomedical Technologies (Stoughton, Mass.). TGFβ-1 was obtained from R & D Systems (Minneapolis, Minn.). Sources of other growth factors, hormones, and chemicals were as described elsewhere (9,10)

METHODS

Unless otherwise specified, the methods used for the cloning procedures were the standard methods described in Sambrook, J., Fritsch, E. F., and Maniatis, T., Molecular Cloning: A Laboratory Manual (Cold Spring Harbor Laboratory, NY, 1989. This reference details the following methods: Plasmid DNA purification, phenol extraction of DNA, ethanol precipitation of DNA, restriction endonuclease reactions, agarose gel electrophoresis, purification of DNA fragments from agarose gels, and transformation of E. coli cells.

The TGFβ-induced cDNA library (FIG. 2) was prepared by using The Librarian II cDNA Library construction System from Invitrogen. The MaxBac TM baculovirus expression system was used to produce the MPS-1 protein of the invention in accordance with the procedures described in MaxBac Baculovirus expression system Manual, version 1.3 (In vitrogen).

Construction of vectors containing the coding sequence of the invention was performed using ligation techniques as described by Sambrook et al, 1989. After isolation, plasmids were cut and the DNA fragments of interest adapted and religated to produce the plasmids required. Cleavage was performed by treating with restriction enzymes in an appropriate buffer. After completion of the reactions, protein was eliminated by extraction with phenol and chloroform, and the DNA was recovered from the aqueous solution by precipitation with ethanol. After construction, plasmids were analyzed by restriction enzymes and PCR (37) with appropriate primers for ST1H2 (5' AAG GAA CAT CCT TCT GTA AGC 3' (complementary to nucleotides 236–256 of SEQ. ID No:1) and 5' ATG CCT CTC GCA AAG GAT CTC 3'(Nucleotides 21–41 of SEQ. ID No:1)) and/or polyhedrin gene (18). Sequencing was done by using Sequenase Version 2.0 DNA Sequencing Kit (U.S. Biochemical Co., Cleveland, Ohio).

EXAMPLE 1

Preparation of cDNA Library

Total cellular RNA was isolated from human mammary carcinoma MDA-468 cells after treatment with TGFβ (2.5 ng/ml) for 3 hours by the guanidinium method (7). Poly $(A)^+$ RNA was prepared from pooled aliquots of total cellular RNA using oligo(dT)-cellulose chromatography (The Fast Track RNA isolation kit, In vitrogen, San Diego, Calif.).

A cDNA library was constructed in the vector pcDNA-II (Invitrogen). Library construction was based on a modified Gubler-Hoffman cDNA synthesis procedure using the Librarian II (Invitrogen). The steps used during that process are shown in FIG. 2A. Briefly, first strand cDNA synthesis was performed on 5 ug of poly$(A)^+$ RNA using reverse transcriptase essentially as described by Gubler and Hoffman (Gene, 25:263,1983). Second strand synthesis was performed with 4 U of RNase H, which cleaves RNA while in hybrid RNA-DNA form, and 100 U of DNA polymerase I, which then uses the fragments of nicked RNA as primers to synthesize the second strand of cDNA. DNA ligase was added to repair any nicks in the double-stranded DNA. T4 DNA polymerase(10 ug) was used to remove 3' overhangs, creating blunt ends. BstX I non-palindromic linkers, having the sequences 5' CTTTAGAGCACA 3' and 3' GAAATCTC 5' were added to the double-stranded, blunt-end cDNAs. Double-stranded cDNA was subjected to electrophoresis to select for cDNAs longer than 500 bp and to remove unreacted linkers. The selected cDNAs were removed from the agarose gel slice by electroelution. cDNAs were ligated into the BstX 1 cut pcDNAII (3.0 kb) vector and transfected into component E. Coli INVIα F' cells as described by Invitrogen. The transformed cells containing the cDNA library were stored frozen until the time of screening. About 1.6 million distinct cells were created, each having a cDNA insert from the MDA-468 cells that have been treated with TGFβ.

EXAMPLE 2

Preparation of Probes and Screening of cDNA Library.

This example describes the differential hybridization screening process that allowed the identification of the clonal colony containing the cDNA sequence of the invention. The main steps used for differential hybridization are shown in FIG. 2B and are briefly described as follows.

In order to screen the library, mRNA probes were prepared using mRNA from either (1) untreated MDA-468 cells, or (2) MDA-468 cells that had been incubated with 2.5 ng/ml TGFβ for 3 hours. Polyadenylated mRNA was purified as described in Example 1, and an isotope of phosphorus (gamma $^{32}P$) was incorporated into the mRNA using labelled adenosine triphosphate (ATP) and T4 polynucleotide kinase. The TGFβ-induced and uninduced mRNA's had approximately equal specific activity after labelling.

The transformed E. coli cells from the library were streaked onto solid agar nutrient in Petri dishes and incubated for 16 hours at 37° C. to allow individual cells to grow into clonal colonies. Three nitrocellulose filters were then sequentially pressed against each Petri dish. Each filter picked up cells from the clonal colonies on the agar plates, and the cells that clung to the filters were grown in liquid nutrient (which permeated the porous filter paper) until they established clonal colonies which appeared on visual inspection to be of suitable size and density. For each plate, one of the three filters was stored as a master to preserve the colonies in the same spatial arrangement as the two screening filters. The Petri dishes were also preserved.

This process created two identical filters for screening, so that for each agar plate, a first filter could be screened using radiolabelled mRNA probes from TGFβ-treated cells, and a second identical filter could be screened using radiolabelled mRNA probes from untreated cells.

Both sets of filters were treated with sodium hydroxide to break up the E. coli cells and to denature the DNA to generate single-stranded DNA. Subsequently, the DNA was cross-linked to the filters by UV light irradiation for 96 seconds. Each filter was then incubated with a radiolabelled probe from either TGFβ-treated or untreated cells at 42° C. for 16 hours to allow the probes to hybridize to the affixed single-stranded DNA if their sequences were complementary. The unattached mRNA was washed off by rinsing in 2× standard saline citrate buffer (SSC; 0.15M sodium chloride, 0.015M sodium citrate, pH 7.4) at 55° C.

After the radiolabelled probes were hybridized to the filters in this manner, the filters were exposed to autoradiographic film, to indicate where the probes had become affixed to the filters. A dark spot on an autoradiograph indicated that a high concentration of radioactive probe had become attached to the filter at that location.

This screening process allowed the identification of clonal colonies containing cDNA sequences which annealed to mRNA probes from cells treated with TGFβ, but which did not anneal to mRNA probes from untreated cells. This was done by comparing autoradiographs from duplicate paired filters, both visually and using a computerized video system (the JAVA system, sold by Jandel, Corte Madera, Calif.). In the great majority of the clonal colonies, the locations of the dark spots were identical on any two paired filters. However, in a small number of instances (involving 40 clonal colonies out of 8,000 colonies that were screened in this manner), a dark spot appeared on the plate that had been screened with mRNA from cells treated with TGFβ, while no corresponding dark spot was generated by probes from the untreated cells. That difference indicated that the cDNA vector which had been inserted into that particular colony of cells contained an mRNA sequence that had been stimulated by TGFβ treatment.

The positions of those forty colonies of interest were identified, and viable colonies having the same plasmids were obtained from the third set of filter lifts, which had been refrigerated. The colonies of interest were given arbitrary designations, depending on which filter they were located on and their location on the filter.

One specific clonal colony, designated as the ST1H2 colony because of its position on a specific filter, was analyzed in detail because it contained a cDNA sequence of interest. Additional work using Northern blot analysis of total RNA from MDA-468 cells confirmed that the ST1H2 clone contained a cDNA sequence that was induced by TGFβ. This cDNA, hybridized to a relatively small MDA-468 cellular mRNA having a length of about 350 bases.

The cDNA sequence carried by the ST1H2 clone was later designated as the MPS-1 sequence. However, that did not occur until substantially later, after the characteristics of the protein encoded by the cDNA became clear.

EXAMPLE 3

Sequencing of the cDNA Carried by the ST1H2 Clone

In order to sequence the cDNA carried by the ST1H2 clone, an M13 viral vector was used. M13 viruses are widely used in genetic engineering, since the genes carried by M13 viruses go through a single-stranded stage in infected bacterial cells during the viral replicative cycle. This allows for single-stranded DNA having an unknown sequence to be reproduced and purified fairly simply, in relatively large quantities. Various kits which contain M13 capsid proteins and a helper phage are commercially available. These kits allow a plasmid having an M13 origin of replication to be incorporated into a functional M13 virus, which can then be used to infect bacterial cells.

The pcDNAII cloning vector, which was used to create the ST1H2 clone, contains an M13 origin of replication. This allowed the ST1H2 plasmid DNA to be transferred to an M13 virus, using a helper phage designated as R408 (Invitrogen). The M 13 viruses were used to infect bacterial cells, and while the viral DNA was in the single-stranded phase in the bacterial cells, the cells were lysed and single-stranded DNA was purified. This allowed the single stranded DNA to be sequenced by the dideoxy chain termination method of Sanger et. al. (48) using Sequenase (Version 2.0) and –40 M13 primer.

The nucleotide sequence for the cDNA insert carried by the ST1H2 clone is shown in FIG. 3. The coding sequence starts at nucleotide 21 and ends at nucleotide 273, with a TGA stop codon followed by the 3' untranslated region. The open reading frame continues up to the polyadenylate region of this cDNA which starts at position 330 (not shown). The ATG codon for the methionine residue at position 21 is preceded by an A at the 3-position and is immediately followed by a C residue. These features are compatible with initiation codons of some mRNAs of higher eukaryotes (30). On the basis of initiation at site 21, the MPS-1 protein is 84 amino acids long with an unmodified molecular size of 9,460 Daltons.

EXAMPLE 4

Computer Correlation with Zinc Finger Proteins

After the cDNA and amino acids sequences of the protein encoded by the ST1H2 clone were known, the Inventor used a computer to search DNA and protein sequence databases maintained by the National Institutes of Health (NIH; Bethesda, Md.) and the European Molecular Biology Laboratory (EMBL; Heidelberg, FR of Germany), using NIH and EMBL data stored on compact disc-read only memory (CD-ROM) devices (sold by Hitachi; discussed in reference 31). That computerized search revealed that the MPS-1 sequence has some homology with a DNA transcription factor designated as TFIIIA from Xenopus laevis (a species of frog widely used in genetic studies because of certain chromosomal characteristics). TFIIIA protein has nine zinc finger domains.

After the initial computerized search revealed the homology with the X. laevis TFIIIA zinc finger protein, a review of the amino acid sequence of the human protein expressed by the ST1H2 clone indicated that the ST1H2 sequence has four cysteine residues in sequence as follows:

—Cys—$X_2$—Cys—$X_{15}$—Cys—$X_2$—Cys— where $X_2$ and $X_{15}$ refer to sequences of two and fifteen residues, respectively, as shown in FIG. 1. This configuration allows the cysteine residues to form a tetrahedral complex with a zinc ion, in a manner that causes the amino acid residues in the $X_{15}$ segment to protrude in a "finger" configuration. This arrangement occurs in a number of "zinc finger" proteins and reportedly provides structural stability to the finger conformation (28). The zinc finger domain of the protein encoded by the ST1H2 clone includes (with all four cysteine residues) amino acid residues 37 through 59; those residues were encoded by nucleotides 129 through 197 in the cDNA (FIG. 4).

After the zinc finger characteristic of the ST1H2-encoded protein was recognized, the Inventor did a second NIH and EMBL database search which focused solely on proteins that had been reported to be zinc finger proteins. The second computerized search disclosed varying levels of homology with a number of zinc finger proteins; the highest degree of homology detected indicated that 52.7% of the nucleotides in the MPS-1 cDNA correlated with nucleotides in a gene that encoded a Xenopus laevis protein designated as XELZNF5.

Additional computerized analysis of the amino acid sequence of the newly discovered protein indicated that it contains a hydrophilic region near the N-terminus, starting at amino acid 7 and ending at 24 (FIG. 5) (21). It also contains a hydrophobic region from position 40 to 65 (FIG. 5). Furthermore, the C-terminal region is hydrophilic around position 80 (FIG. 5). From these results it can be inferred that the MPS-1 sequence encodes an amphipathic protein. The amphipathic characteristic of the protein tends to help the protein be transported through lipid membranes, which is essential if the protein expresses its activity either inside the nucleus (by interacting with chromosomes) or in the extracellular fluid (by interacting with cell surface receptors).

After recognizing both the zinc finger domain and the amphipathic characteristic of the newly discovered protein, the Inventor arranged a series of tests which confirmed that the protein is in fact localized within the nucleus and/or secreted into the extracellular fluid. Those tests are described below, in Example 8; autoradiographs of gels which confirm this analysis are provided in FIG. 8.

EXAMPLE 5

Construction of Baculovirus Expression Vector Encoding Fusion Protein MPS-1/P17

In order to generate substantial quantities of the newly discovered protein in eukaryotic host cells, and in order to enable studies on the localization and activities of the protein in eukaryotic cells, the human-derived cDNA was removed from the pcDNA-II-ST1H2 plasmid and inserted into a transfer vector suitable for transforming insect cells. Various studies have indicated that many mammalian proteins expressed in insect cells are correctly folded and contain post-translational modifications normally found in mammalian cells, including glycosylation (the addition of sugar moieties to the amino acid residues of the protein).

One insect cell transformation vector that is commercially available in a convenient kit involves a baculovirus vector described in U.S. Pat. No. 4,745,051 (Smith and Summers) and in Luckow and Summers (18). The kit (which is sold by Invitrogen of San Diego, Calif.) uses Spodoptera frugiperda (Sf9) insect cells as eukaryotic host cells to express genes carried by the baculovirus expression vector. The strain of baculovirus initially used to prepare the expression vector of the kit was an Autographa californica nuclear polyhedrosis virus (AcNPV). The wild-type virus was modified to give it several new characteristics, including (1) a DNA insertion site that places an inserted foreign DNA sequence under the control of the strong polyhedrin promoter, (2) an E. coli orgin of replication, so that the vector can be cloned as a plasmid in E. coli or certain other bacterial cells if desired. The modified transfer vector is referred to in advertisements by the trademark "pBlueBac", since it carries a marker gene that causes transformed cells to appear as blue plaques when grown on certain types of solid nutrient media. One of the pBlueBac viral vectors is referred to in scientific articles as pJVETL.

The steps used to transfer a 0.4 kilobase (kb) segment of human-derived cDNA out of the pcDNA-II-ST1H2 plasmid and into the pJVETL vector are shown in FIG. 6. In one series of reactions, the E. coli cells were lysed and the ST1H2 plasmid was purified by cesium chloride (CsCl) density gradient centrifugation to remove chromosomal DNA. The purified plasmid was digested with SpeI and XbaI, which cleaved the plasmid at cleavage sites supplied by the pcDNA-II cloning vector. The SpeI and XbaI cleavage sites were outside of the cDNA insert, which was bracketed by BstXI cleavage sites.

The DNA fragments that resulted from the SpeI and XbaI digestion were size-separated using gel electrophoresis, and a double-stranded 0.4-kb fragment (which contained the human-derived cDNA) was eluted from the gel for further use. The 0.4 kb fragment contained the complete MPS-1 coding region as well as 20 base pairs of 5' untranslated sequence and 56 base pairs of 3' untranslated sequence.

In a separate set of reactions, the pJVETL viral vector was digested with NheI, which generates overhangs that are compatible with both XbaI and SpeI overhangs. The Nhe I digestion effectively linearized the plasmid without removing any DNA from it.

The linearized plasmid was mixed with the 0.4 kb fragment from the ST1H2 plasmid, and the DNA fragments were ligated using T4 ligase. This generated a variety of recombinant plasmids that were transfected into and grown in clonal colonies of E. coli INVI αF' cells. Forty sets of clonal cells were lysed and their plasmid DNA was purified and analyzed so that a clonal line having a vector with the desired structure could be selected. A desired recombinant vector was identified and initially designated as pJVETL-ST1H2. Subsequently, after more information became available on that vector and on the proteins it encoded (as discussed below), it was renamed as the pJVETL/MPS-1/P17 vector, as shown in FIG. 6.

The proper orientation of the ST1H2 insert in the pJVETL vector was confirmed by polymerase chain reaction (PCR) using combinations of both one polyhedrin primer (18) and two ST1H2 primers. The ST1H2 primer sequences were selected based on a computerized analysis, using the "OligoPrimer" software (described in W. Rychlik 1990 and sold by National Biosciences, Hamel, Minn.). That computerized analysis indicated that optimal hybridization of these primers to the target sequence will occur. PCR analysis was done using a DNA Thermal Cycler (Perkin Elmer Cetus, Norwalk, Colo.). Proper orientation of the insert in clones selected for further work was also confirmed by restriction enzyme mapping. Nine out of forty clones had the ST1H2 sequence in the proper orientation.

The pJVETL/MPS-1/P17 vector expressed two distinct but related proteins: 1. a peptide containing the wild-type form of the MPS-1 protein, as shown FIGS. 1, and, 2. a fusion peptide which contained the MPS-1 sequence coupled to 17 additional amino acid residues at the N-terminus, due to an in-frame start codon (ATG) present in the pcDNA-II 5' linker used to make the cDNA library (Table 1). This fusion peptide was referred to as the MPS-1/P17 peptide.

EXAMPLE 6

Construction of Baculovirus Expression Vector Encoding Natural Form MPS-1 Protein To avoid possible complications arising from the presence of the fusion peptide, and to increase the expression of the natural form (NF) unfused MPS-1 protein, the recombinant vector pJVETL/MPS-1/P17 was modified to delete the spurious start codon. The steps and results of this modification are summarized in FIG. 7 and Table 2 and was accomplished as follows.

The plasmid from the ST1H2 clone was cut with restriction enzymes XhoI and SpeI, the 400 bp fragment was isolated in a 1% Sea Kem gel using Tris acetate-EDTA (TAE) buffer, and the DNA was purified using Geneclean (BIO 101 Inc., La Jolla, Calif.). Then, 2 ug of the 400 bp ST1H2 DNA was treated with 5 units of T4 DNA polymerase in a solution containing 66 mM TRIS pH 7.6, 5 mM $MgCl_2$, 5 mM DTT and 100 mM of each dNTPs, to convert the single-stranded overhangs into blunt-ended termini. The reaction was at 12° C. for 15 min, followed by heating at 70° C. for 10 min. The solution was extracted in phenol/chloroform (1:1), followed by chloroform extraction and DNA precipitation with 3M sodium acetate and ethanol.

Subsequently, hemiphosphorylated double-stranded NheI adapters having the following sequences:

5' HO-CTAGCCCGGG 3'

3'GGGCCC-$P0_4$5' were ligated to the blunt-ended ST1H2 fragments using 2 Weiss units of T4 DNA ligase per 0.5 ug of blunt-ended DNA in a solution containing 66 mM Tris Cl, pH 7.6, 5 mM $MgCl_2$, 5 mM DTT, 0.5 mM ATP, and 200 ng NheI adapters. The reaction mixture was incubated overnight at 16° C. This caused NheI-compatible 5' overhangs to be added to the ends of the blunt-ended cDNA fragments.

The following day, the ligase enzyme was inactivated by heating at 65° C. for 15 min. The solution was chloroform/phenol (1:1) extracted, followed by chloroform extraction and DNA precipitation with 3M sodium acetate and ethanol.

After the addition of the NheI adapters, the 0.4 kb cDNA segments were reacted with 18 units of T4 polynucleotide kinase to phosphorylate the 5' NheI overhang, in a solution containing 66 mM Tris-HCl (pH.7.6), 10 mM $MgCl_2$, 10 mM DTT, and 1.0 mM ATP. The mixture was incubated for 1 hr at 37° C. Then, the solution was chloroform/phenol (1:1) extracted, followed by chloroform extraction and DNA precipitation with 3M Na acetate and ethanol.

Gel electrophoresis for sizing and removal of adaptors was done in 3% Nu Sieve agarose (FMC Bio-Products, Rockland, Me.) using TAE Buffer. The gel slice containing the 400 bp ST1H2 DNA fragment was melted to free the DNA, and the 400 bp ST1H2 DNA having NheI overhangs was ligated to the pJVETL DNA which had been cleaved with NheI, using 2 Weiss units of T4 DNA ligase in a solution containing 50 mM Tris HCl (pH 7.6), 10 mM Mg $Cl_2$, 10 mM DTT, and 10 mM ATP at 25° C. for 16 hours.

Subsequently, INVI αF' E. coli cells were transfected with the ligated plasmids as described in Example 5. The transfected cells carrying the desired plasmids were selected by means of the Ampicillin resistance gene carried by the pJVETL vector and the plasmids were analyzed by both PCR and restriction enzyme mapping as indicated in Example 5.

This series of steps generated a vector that was designated as the pJVETL/MPS-1/NF1 vector, where "NF1" refers to the natural form MPS-1 protein. Since the spurious in-frame start codon present in the pcDNA-II vector was eliminated, the ATG start codon which begins at nucleotide position 21, shown in FIG. 3 and Table 2, is the first start codon downstream of the polyhedrin viral promoter carried by the pJVETL vector. Therefore, in insect cells, the pJVETL carrying the XhoI/SpeI-digested cDNA fragment from the ST1H2 plasmid produces a protein identical to the native unprocessed protein present in mammalian cells.

EXAMPLE 7

Use of the Baculovirus Vectors to Express MPS-1 Protein in Insect Cells

To transfer either the fused or unfused MPS-1 gene into the baculovirus genome, either the pJVETL/MPS-1/P17 or the pJVETL/MPS-1/NF1 plasmid was co-transfected with wild-type AcNPV viral DNA into Sf9 cells. The Sf9 cells were cotransfected with 1 ug of the wild-type AcNPV baculovirus genomic DNA and 2 ug of plasmid DNA, by the calcium phosphate transfection method (18). Two days after transfection, extracellular virions were collected and allowed to form plaques on Sf9 cells. This process follows the procedures set forth in Summers and Smith, 1988.

Polyhedrin-negative blue plaques were picked and used to infect Sf9 cells in 24-well cell culture plates. Cells were lysed and screened by PCR using appropriate primers, and the results were confirmed by Northern blot hybridization with a ST1H2 probe. Recombinant virus was further purified by performing two more rounds of plaque purification. Stocks of recombinant virus were grown on Sf9 cells to a titer of $10^7$ to $10^8$ PFU/ml for use in all subsequent experiments.

EXAMPLE 8

Studies on Protein Localization in Insect Cells

The pJVETL/MPS-1/P17 vector, prepared as described in Example 5, was used to study the localization of the MPS-1 protein and the MPS-1/P17 fusion peptide in Sf9 cells, which are eukaryotic. These studies were carried out using the following method. Sf9 cells were seeded at a density of $6\times10^5$ cells per 16-mm well in complete Grace medium and infected at a multiplicity of 10 viral particles per cell with recombinant baculovirus carrying the MPS-1/P17 gene. At 72 h postinfection, the cells were labeled for 5 h with [$^{35}$S]cysteine (50 uCi/ml) in cysteine-free Grace medium containing 5 uM $ZnCl_2$. This caused protein which was being actively synthesized by the cells to incorporate the radioactive amino acid in the protein.

After labelling, the cells were treated in varying manners, depending on what was being analyzed. Some cell cultures were centrifuged, and the cell-free supernatant liquids were analyzed to determine whether labelled proteins were being secreted by the cells into the extracellular fluid. In other cases, the cells were lyzed and processed to isolated either cytoplasmic or nuclear extracts, using the methods described in reference 50.

Figure 8A:
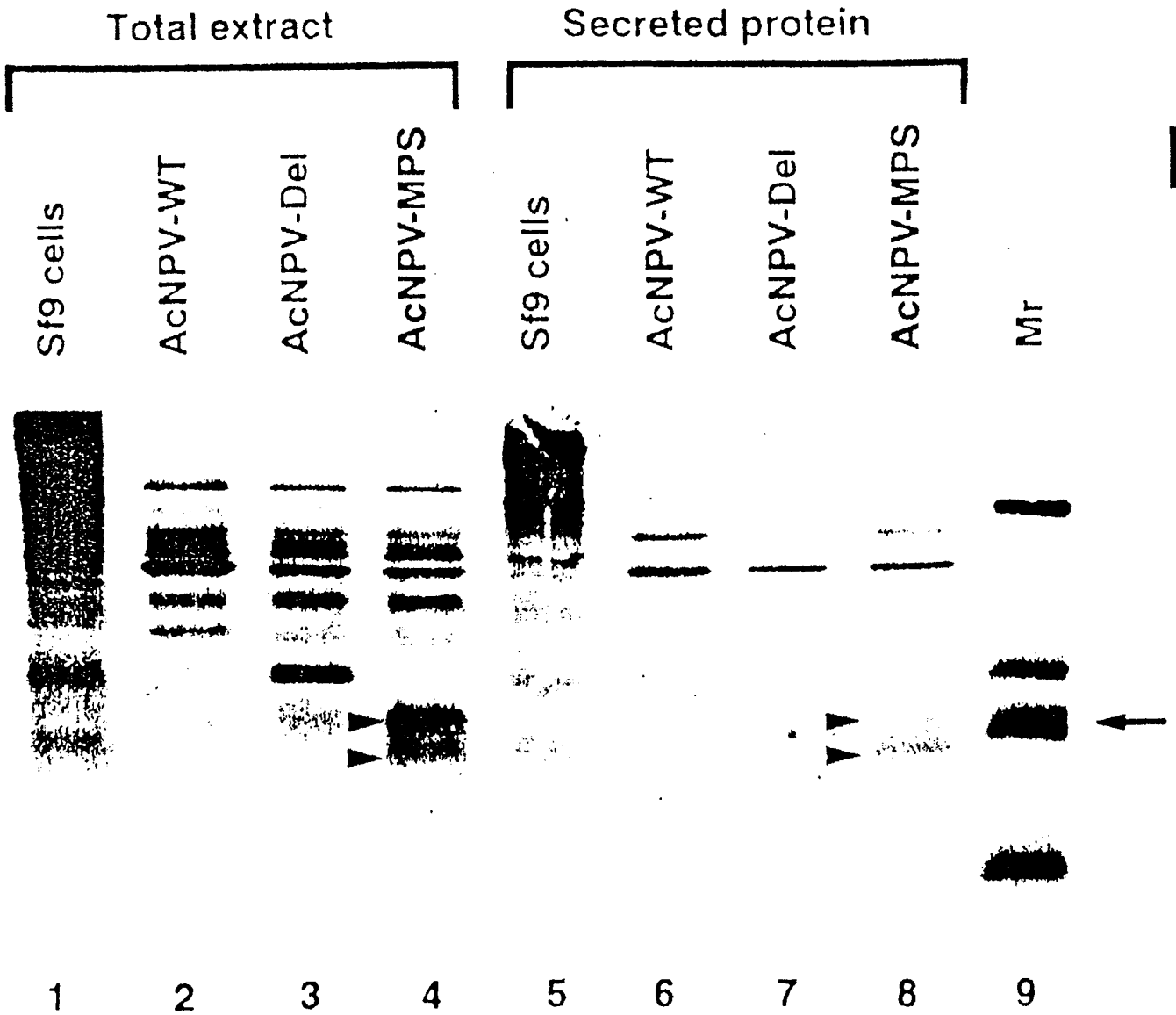
FIG. 8 shows the electrophoresis of radiolabelled MPS-1 protein from Sf9 insect cells that were infected with a viral vector containing the MPS-1/P17 gene. The top photograph (FIG. 8A) shows total cellular protein (lanes 1–4) and secreted (extracellular) protein (lanes 5–8). As indicated by the two MPS-1 bands in lane 8, a substantial quantity of MPS-1 is secreted by the cells. The lower band (smaller protein) is endogenous MPS-1 protein; the upper band is a variant having an additional 17 amino acids at the N terminus. The bottom photograph (FIG. 8B) shows protein isolated from the non-nuclear cytosol (lanes 10–13) and from the nucleus (lanes 14–17). As indicated by the absence of MPS-1 bands in lane 13 (cytosol) and the heavy MPS-1 bands in lane 17 (nucleus), the great majority of MPS-1 inside the cell is transported into the nucleus.
Figure 8B:
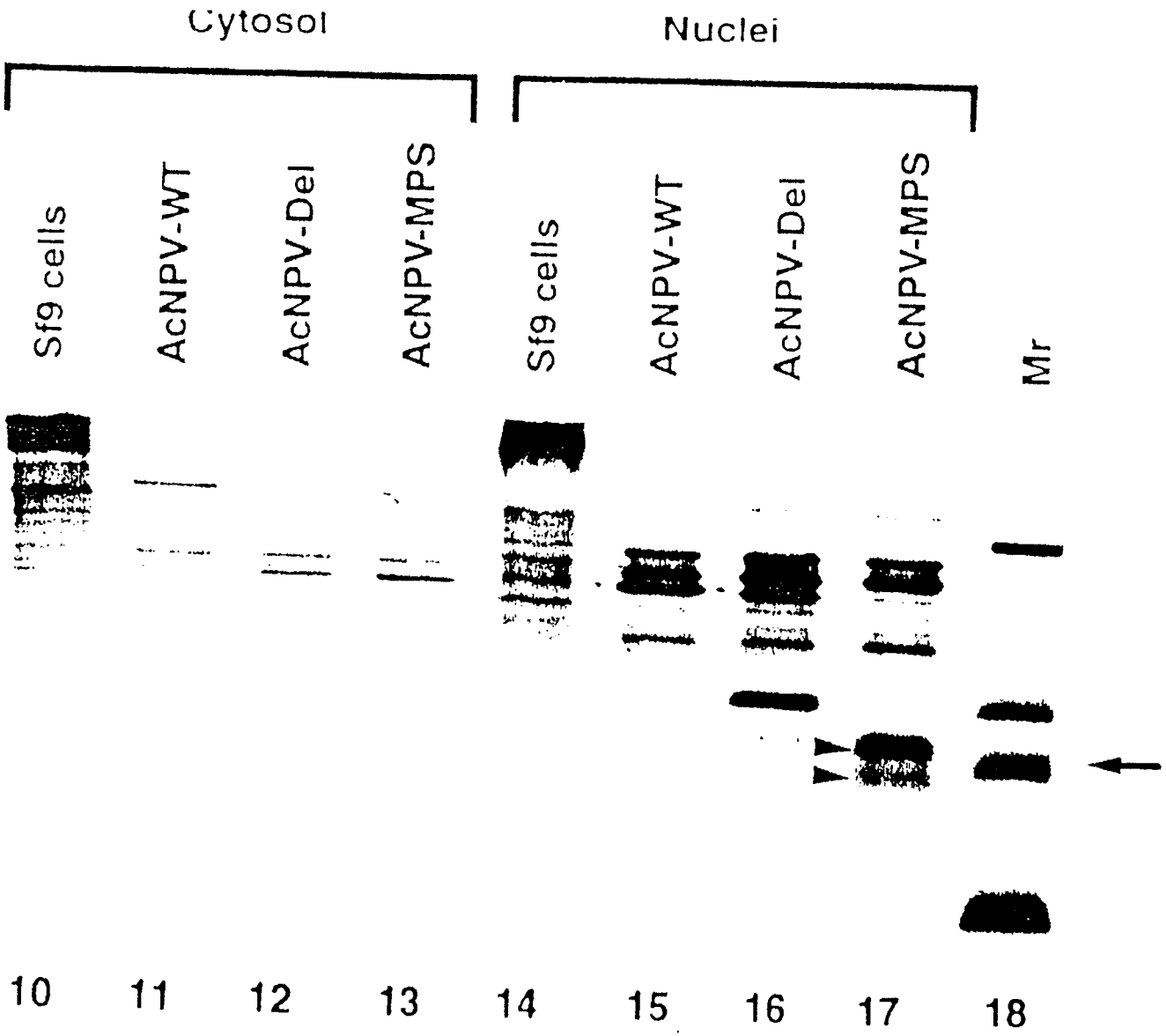

In all cases, the isolated fluids were processed by electrophoresis, to separate the protein mixtures into bands depending on molecular weights, which could be ascertained by means of "size markers" (radiolabelled DNA fragments having known sizes, designated as Mr in FIG. 8). Then, the gels were autoradiographed.

The results, shown in FIG. 8, clearly indicate several important characteristics of both the natural form MPS-1 protein and the fused MPS-1 protein having 17 extra amino acids. First, as indicated by the heavy double bands (marked by arrowheads) in lane 17, most of the MPS-1 protein is localized in the nucleus of the cell. Clearly, both the natural form and the fused protein are transported inside the nucleus.

Second, as indicated by the lighter but still substantial double bands (with arrowheads) in lane 8, a substantial portion of the natural and fused MPS-1 proteins are secreted by cells into the extracellular fluid. If Metallopanstimulin receptors exist on the surfaces of cells, the active secretion of the natural MPS-1 protein would allow the protein to interact with receptors on the surfaces of either (1) the same cells that generate and secrete the protein (autocrine stimulation) or (2) other cells which have such receptors (paracrine stimulation).

Third, the absence of a heavy band indicating either natural or fused MPS-1 in the cytosol (the fluid inside the cell but outside of the nucleus) suggests that any transport mechanisms that cause the protein to be taken into the nucleus or secreted by the cell are relatively efficient. Since the protein is initially translated from mRNA into protein in the cytosol, one would expect to find a significant quantity in the cytosol unless it is efficiently transported out of the cytosol to its intended destination.

Analysis of cell extracts by electrophoresis under reducing conditions showed two labeled proteins of about 10,000- and 13,000-Da corresponding to the natural form MPS-1 and the MPS-1/P17 proteins, respectively, in cells infected with the recombinant virus containing the MPS-1 sequence (FIG. 8, lane 4). These proteins, were not detected in extracts from cells infected with AcNPV-Del, a virus in which the MPS-1 gene was deleted (FIG. 8, lane 3). Maximal levels of MPS-1 protein production, which represents about 15% of total cellular protein, were observed at 72 h after infection.

The secretion of recombinant MPS-1 protein into the extracellular culture fluids (FIG. 8) provides an enriched source, greatly facilitating subsequent purification. However, it should be noted that the protein is also present in large quantities in the nucleus of Sf9 cells (FIG. 8) and can be recovered from the nucleus by utilizing standard procedures as described (2,9,50).

EXAMPLE 9

Effects of MPS-1/P17 on Growth of Human Cultured Cells.

The ability of MPS-1/P 17 to induce growth effects in culture cells was determined using MDA-468 human mammary carcinoma cells, SK-MEL-28 human melanoma cells, and WI-38 human normal diploid fibroblasts. The assay was performed on monolayer cells grown in Dulbecco-Öogt modified Eagle's medium supplemented with 5% fetal calf serum (v/v) as previously described (1,6). The MPS-1/P 17 protein was purified from Sf9 insect cells by high-performance liquid chromatography and was added directly to the culture medium. The cell number was determined after trypsinization of cells on day 3 of culture by Coulter-counter measurements (1).

The MPS-1/P17 protein stimulated the growth of MDA-468 cells at 25 to 50 ng/mL. The stimulation of MDA-468 cell growth at 72 hours was 35% with 50 ng/mL MPS-1/P17 in comparison to control untreated cells.

The growth of SK-MEL-28 human melanoma cells was inhibited in a dose-dependent manner by 25 to 100 ng/mL MPS-1/P17. After 24 hours of exposure to MPS-1, SK-MEL-28 cells began to appear granular, numerous cells floated into the culture medium, many cells were destroyed and no mitotic cells were observed. After 72 hours of exposure to MPS-1/P17, the decrease in cell number of treated cells with respect to control untreated cells was about 33% in cells treated with 100 ng/mL MPS-1/P17.

Under similar experimental conditions, no growth effects or cytotoxicity (as determined by cell granularity, floating or dead cells) was observed in WI-38 human diploid fibroblasts treated with 25 to 100 ng/mL MPS-1/P17.

These results suggest that the MPS-1/P17 protein is a bifunctional regulator of cell growth (6,11) as indicated by the fact that MPS-1/P17 inhibits the growth of SK-MEL-28 cells, at concentrations similar to those that stimulate the growth of MDA-468 cells.

EXAMPLE 10

Preparation of Anti-MPS-1 Antibodies Using Synthetic Peptides with Partial MPS-1 Sequences Antibodies which bind to the MPS-1 protein have been generated using several different techniques. During the early stages of the work, after the amino acid sequence of the protein was deduced from the cDNA sequence but before the protein had been purified from eukaryotic host cells, such antibodies (in a polyclonal mixture) were generated using synthetic peptide sequences. That work is described in this example. Other work involving the purified MPS-1 protein is described in Example 11.

Three different amino acid sequences were used (FIG. 3). One sequence, PLAKDLLHPSPEEEKR (using the one-letter amino acid code), corresponds to MPS-1 amino acid residues 2–17 (SEQ. ID NO: 2) was designated as the A1 peptide. It was derived from the N-terminal region of the peptide, located between the N-terminus and the zinc finger domain, as shown in FIG. 3.

A second synthetic peptide used as an antigen had the sequence YKITTVFSHAQTVVL, which corresponds to MPS-1 amino acid sequence 41–55 (SEQ. ID NO:2), in the zinc finger domain. That peptide was designated as the A2 peptide.

A third synthetic peptide had the sequence TGGKARLTEGCSFRRQH, which corresponds to MPS-1 amino acid sequence 67–84 (SEQ ID NO:2), located between the zinc finger and the C-terminus as indicated in FIG. 3. It was designated as peptide A3.

All three peptides were synthesized on an Applied Biosystems peptide synthesizer (Model 430A) using ter-butyloxycarbonyl (t-boc) chemistry.

The A1 (N-terminal) and A3 (C-terminal) peptides were selected so that they would not contain any portion of the zinc finger domain of the MPS-1 protein, because the zinc finger domain is a highly conserved structure and antisera against it might cross-react with other zinc finger proteins. However, antibodies which bind to the zinc finger domain of MPS-1 may be useful for studying relationships between MPS-1 and other zinc finger proteins, as well as for diagnostic studies.

The A1, A2 or A3 peptides, to which a cysteine moiety was added at the N-terminus, were crosslinked to a protein which stimulates the immune system, keyhole limpet hemocyanin (KLH) by the use of sulfosuccinimidyl 4-(N-maleimidomethyl) cyclohexane-1-carboxylate (Pierce, Rockford, Ill.).

To produce anti-peptide antibodies, three New Zealand rabbits were immunized by subcutaneous injection with 300 ug each of the A1, A2, or A3 peptide-KLH complex and Freund's complete adjuvant(Difco). The rabbits were given a booster injection (150 ug) after 3 weeks and bled at 4 weeks. The sera obtained from the injected rabbits were screened for anti-peptide antibodies by ELISA on peptide-coated polyvinylchloride 96-well plates (5). Sera from the three rabbits were positive for anti-peptide antibodies. Subsequently, booster injections were given as needed. The sera was obtained by centrifugation and the antibodies were purified as described below.

The anti-peptide antisera were affinity purified before use by passing it over a column containing the respective peptide coupled to cyanogen bromide-activated Sepharose beads (Pharmacia, Piscataway, N.J.). The immunoglobulins which bound to the columns were eluted with 4M $MgCl_2$, and eluted fractions were dialyzed against phosphate-buffered saline.

The polyclonal antibodies were tested for reactivity to the A1, A2, or A3 peptides by the following techniques: (1) immunoprecipitation (2,5); (2) immunoblot analysis (3,4); and (3) peptide-coated polyvinylchloride 96 well plates (5).

The affinity-purified antibodies recognized two proteins of 10- and 13-kDa in extracts from S. frugiperda cells infected with the AcNPV-MPS-1/P17 viral vector containing the MPS-1 cDNA sequence but not in extracts from cells infected with the AcNPV vector without the MPS-1 insert.

These polyclonal antibodies, designated anti-A1, anti-A2 and anti-A3, were used to detect MPS-1 protein in various tissue specimens and cells as described in Example 12. It should be pointed out that they were interchangeable for the purpose of determining the presence of MPS-1.

EXAMPLE 11

Preparation of Polyclonal Antibodies Using Purified MPS-1 Protein

To produce anti-MPS-1 polyclonal antibodies, two rabbits were inoculated subscapularly with MPS-1 protein (100 ug in each rabbit). The protein was produced by transformed Sf9 insect cells as described above, purified by polyacrylamide gel electrophoresis, and mixed with an equal volume of Freund's complete adjuvant. The rabbits were given a booster injection after 4 weeks and bled at 6 weeks. The sera obtained from the injected rabbits were screened for anti-MPS-1 antibodies by ELISA on MPS-1-coated polyvinylchloride 96-well plates (5). Sera from both rabbits were positive for anti-MPS-1 antibodies. The sera was obtained by centrifugation and the antibodies were purified as follows.

The anti-MPS-1 antisera were affinity purified before use by passing it over a column containing the MPS-1 protein coupled to cyanogen bromide-activated Sepharose beads (Pharmacia, Piscataway, N.J.). The immunoglobulins which bound to the columns were eluted with 4M $MgCl_2$, and eluted fractions were dialyzed against phosphate-buffered saline.

The polyclonal antibodies obtained in this manner were screened for binding activity against the MPS-1 protein by the methods described in Example 10.

The affinity-purified anti-MPS-1 antibodies recognized two proteins of 10- and 13-kDa in extracts from S. frugiperda cells infected with the AcNPV-MPS-1/P17 viral vector containing the MPS-1 cDNA sequence but not in extracts from cells infected with the AcNPV vector without the MPS-1 insert.

For subsequent diagnostic work, the purified polyclonal antibodies obtained from either the peptides (Example 10) or the MPS-1 protein were coupled to any of several labelling molecules such as biotin, fluorescein, and radioactive iodine by methods that are well known in the art. Furthermore, the anti-peptide and the anti-MPS-1 antibodies were also detected by using second antibodies labeled with various molecules (e.g.: fluorescein labeled goat-anti rabbit IgG; StrAviGen™ super sensitive universal immunestaining kit, BioGenex, San Ramon, Calif.).

The antibodies generated in this manner and those described in Example 10 have been tested against tissue samples from numerous patients having various types of cancer of ectodermal, mesodermal, or endodermal origin. The antibodies show clear and easily detectable binding to the cancerous cell nuclei in particular, but little or no detectable binding to non-proliferating normal adult human cells. The techniques used for these diagnostic procedures are described in more detail below.

EXAMPLE 12

Diagnostic Uses of Antibodies that Bind to MPS-1

This example relates to immunocytochemical assays performed on cells and tissues to detect the localization of the MPS-1 protein.

For immunoperoxidase labeling (33,34), cultured cells or tissue samples obtained during surgery were fixed overnight in fresh 4% paraformaldehyde, Zenker's, or Bouins solutions. After fixation, tissues were paraffin-embedded using a Fisher Histomatic tissue processor, cut to a 5 um thickness, and affixed to glass slides using Vectabond (Vector Laboratories, Burlingame, Calif.). The sections were deparaffinized, hydrated, and washed in 0.1M phosphate buffered saline (PBS). Endogenous peroxidase activity was blocked by treatment with $H_2O_2$ for 5 minutes. After washing in PBS, the sections were preincubated for 5 minutes with normal goat serum diluted 1:5 in PBS, to decrease non-specific binding. The tissue sections were then incubated with either the rabbit anti-MPS-1 specific antibody diluted 1:50 or a preimmune rabbit serum (control) at 22° C. for 20 minutes. The samples were then incubated at 22° C. for 20 minutes with goat anti-rabbit IgG diluted 1:50, which bound to the rabbit anti-MPS-1 antibodies, if present. Then they were exposed for 20 minutes at 22° C. to Peroxidase rabbit Anti-Peroxidase (PAP) complex (BioGenex, San Ramon, Calif.), which binds to the goat antibody and contains a peroxidase enzyme which enable a chromogenic reaction. After each treatment with antibody, the slides were washed twice with PBS.

The immunohistochemical reaction was developed with freshly prepared 0.05% 3,3-diaminobenzidine tetrahydrochloride(DAB) and 0.01% $H_2O_2$ in 0.05M Tris buffer, pH 7.6 for 10 min. In cells which contained the immobilized PAP complex, the peroxidase enzyme reacted with the $H_2O_2$ to generate free oxygen radicals, which reacted with the DAB to generate a stain allowing it to be assessed visually or using computerized video scanning equipment. The sections were stained with hematoxylin, rinsed with water, and mounted on slides.

Another indirect method used to detect the MPS-1 antigen using anti-MPS-1 antibodies was the Biotin-Streptavidin Amplified system (StrAviGene TM, Biogenex laboratories). In this system, the second antibody link is biotinylated and streptavidin is conjugated to alkaline phosphatase which generates a chromogenic reaction with the appropriate reagents (Naphthol phosphate/Fast Red TR). This affinity staining procedure was performed as described in the instructions provided by the manufacturers (Biogenex).

The results showed intense staining exclusively over the nuclei of cells infected with AcNPV-MPS-1/P17 with no staining in cells infected with the AcNPV-Del, confirming the results obtained by metabolic labeling (FIG. 8). The nuclear localization of the MPS-1 protein was also observed in cultured proliferating cells such as MDA-468 human mammary carcinoma and SK-MEL-28 melanoma cells; in contrast, little nuclear staining was observed in non-proliferating WI-38 human diploid fibroblasts. Furthermore, tissue samples from numerous patients having various types of carcinomas such as ovarian, uterine cervix, endometrial, melanomas, and breast showed significant binding to the cancerous cell nuclei in particular, but little or no detectable binding to non-proliferating normal cells present in the specimens.

EXAMPLE 13

Diagnostic Uses of Biotinylated DNA Probes that Bind to MPS-1 mRNA

The example described here relate to the preparation of biotinylated DNA probes for use in in situ hybridization and Northern blot analysis of MPS-1 mRNA expression in pathological tissue specimens.

DNA probes having the MPS-1 sequence were prepared using polymerase chain reaction (PCR) technology, as discussed in references 37 and 43. The PCR reaction mixture contained two primers (1.0 uM each) having the following sequences, which caused the primers to anneal to DNA sequences within the MPS-1 portion of the ST1H2 clone:

Primer 1: 5' AAG GAA CAT CCT TCT GTA AGC 3 (complentary to nucleotides 236–256 of seq. ID No: 1)

Primer 2: 5' ATG CCT CTC GCA AAG GAT CTC 3'(nucleotides 21–41 of Seq. ID No: 1)

The PCR reaction mixture also contained a gel-purified 400 bp segment with the MPS-1 sequence from the ST1H2 clone (1 ng/100 ul), three of the nucleoside triphosphates (dATP, dGTP, and dCTP) at 200 uM concentration, a fourth triphosphate (dTTP) at 150 uM, and a triphosphate nucleotide coupled to biotin, Bio-11-dUTP (Sigma, St. Louis, Mo.) at 50 uM. Biotin is a protein that binds very strongly to streptavidin; this allowed coupling reactions involving streptavidin to be carried out using the biotinylated DNA probes after the DNA-mRNA hybridization process had been completed.

The PCR reaction was run for 25 cycles. During the reaction, "short product" segments 250 base pairs long having most of the MPS-1 sequence were synthesized. These segments, which were used as probes, contained biotin moieties coupled to each strand at an average density of one biotin moiety every 16 nucleotides.

After completion of the reaction, the probe was purified by chloroform-phenolchloroform extraction. Subsequently, the primers and excess NTPs were removed by a Millipore filter (Low binding cellulose, 10,000 NMWL), with repeated washings in 0.1X Tris-EDTA buffer pH 8.0. The purity of the 250 bp biotinylated MPS-1 probe (in double-stranded form) was confirmed by agerose gel electrophoresis.

Tissue samples from cancer patients were fixed in paraformaldehyde, sectioned, and affixed to glass slides as described in Example 12.

In situ hybridization of the biotinylated probe to the cells (to assess the quantity of MPS-1 mRNA in the cells) was carried out according to the instructions provided in the "In Situ Hybridization and Detection System" (BRL, Geithhersburg, Md.). The formulation of the hybridization solution was 2× standard saline citrate (SSC; 0.15M sodium chloride, 0.015M sodium citrate, pH 7.4), 0.1M sodium phosphate (pH 6.5), 1× Denhardt's solution, 10% dextran sulfate, 50% formamide, 20 mM vanadyl ribonucleoside, and 0.5 ng/ul of the biotinylated MPS-1 probe; the probe was denatured into single-stranded form by heating to 95° C. for 5 min in the hybridizing solution prior to the addition of the vanadyl ribonucleoside. 62 ul of this mixture was added per slide. Each slide was covered with a cover slip and incubated at 42° C. overnight in a humidified chamber. After hybridization, the slides were rinsed by immersion in 3 changes of 0.2× SSC and washed twice in 0.2× SSC for 15 min each at 23° C.

For detection of the MPS-1 sequence, slides were incubated in blocking solution at 23° C. for 15 min, then streptavidin conjugated to alkaline phosphatase (BRL; Gaithersburg, Md.) was added for 15 min. Slides were washed twice for 15 min each in Tris buffer saline and once in alkaline-substrate buffer (BRL) for 5 min. The coloring reagent used was nitroblue tetrazolium (NTB) and 4-bromo-5-chloro-3-indolylphosphate (BCIP). It was prewarmed to 37° C. in alkaline-substrate buffer and added to the slides for 1 hr. Slides were rinsed in deionized water and mounted in glycerol-PBS for microscopic observation. If the alkaline phosphatase enzyme was present in a specific cell, it acted on the NTB and BCIP substrates and a dark color was generated which remained localized within the cell where it was generated.

The cells were examined both visually and using computerized scanning equipment. Visual examinations were made by two independent technicians and were quantitized as follows: O (no reactivity), + (few positive cells), ++ (at least one third of the cells positive), +++ (most cells positive), ++++ (close to all cells strongly positive). Computerized examination was performed using a JAVA video analysis system and the accompanying software (Jandel, Corte Madera, Calif.).

Both neoplastic and stroma cells were observed in tumor samples; the staining recorded referred to that of the tumor cells, since in most cases the stroma cells were not stained at all. The results indicated that intense hybridization occurred (indicating high concentrations of MPS-1 mRNA) in areas of rapid malignant cell proliferation. A gradient of staining was observed, ranging from undifferentiated cells which were darkly stained to differentiated cells which were only lightly stained. Intense hybridization also occurred in the outer regions of cancerous cell masses, corresponding to invasive, rapidly proliferating cells. In most instances, the staining was limited to the cytoplasm of cancerous cells, and no staining was observed in the stroma of the tissues studied. In some cases, the stroma cells stained very weakly in comparison to the tumor cells; these instances usually involved blood vessels present in the tumor.

In addition to distinguishing between cancerous and non-cancerous cells in tissue specimens from a single patient, the mRNA binding assay provided a method of assessing the malignancy of different tumors. As one example, the most intensely stained of all tumors studied was an extremely fast growing melanoma which resulted in the death of the patient in three weeks. In contrast, less malignant tumors showed lesser degrees of staining.

A graph indicating the MPS-1 mRNA concentration determined by Northern blot analysis in a number of tumors is provided in FIG. 9. The highest level of MPS-1 was observed in a vulvar melanoma (>100-fold increase over normal epithelium). High levels of MPS-1 mRNA were detected in endometrial carcinoma, carcinoma of the cervix and breast carcinoma. MPS-1 was also detected in ovarian carcinomas. The MPS-1 was barely detectable in fibrocystic disease of the breast, a benign condition. Normal ovaries, myometrium and rectal muscle were negative for MPS-1. These results correlated well with the staining intensity observed in the in situ hybridization analysis performed on the same samples. Based on information about patient condition and prognosis, obtained from data provided by the physician who treated the patients from whom the various tumor samples were removed, and the type of tumor determined by standard pathological observation, it became clear that the concentration of MPS-1 mRNA correlated with the malignancy of the tumor.

In conclusion, the results of the in situ hybridization assay which detected the presence and concentration of MPS-1 mRNA demonstrated unambiguously that (1) individual malignant cells can be specifically identified in tumor specimens; (2) their degree of proliferation can be quantitatively indicated by the intensity of the probe binding, and (3) the abundance of the MPS-1 mRNA correlates with the pathological degree of malignancy. Thus, the practical use of the MPS-1 sequence results in a superior and highly specific method of diagnosis of malignancy in solid tumors.

EXAMPLE 14

Preparation and Use of Radioactively Labelled DNA Probes that Bind to MPS-1 mRNA In addition to preparing biotinylated DNA probes that could be used for staining or fluorescence assays, radioactively labelled DNA probes were also prepared and tested. The method used by the Inventor involved the same PCR techniques and primers used to create the biotinylated probes described above. To generate a 250 bp double-stranded radioactive segment containing most of the MPS-1 coding sequence, 200 uCi of either dCTP-[$\alpha^{32}$P] or dCTP-[$\alpha^{35}$S] were added to the PCR reaction mixture, and the dCTP concentration was adjusted to 2 uM (49). The 250 bp segment generated as described in Example 13, was added at 1 ng/100 ul and the primers were added at a Final concentration of 1.0 uM each. The PCR reaction was run for 25 cycles and the 250 bp double-stranded radioactive probe was purified in the same manner as the biotinylated probes. Radioactive probes were analyzed by agarose gel electrophoresis and autoradiography. The $^{32}$P-labelled probe was used for Northern and Southern blot analyses of MPS-1 gene expression. The $^{35}$S-labelled probe was used for autoradiographic analyses of MPS-1 mRNA expression in mice embryos. These embryologic studies showed that the MPS-1 sequence is present in greater abundance in cells derived from the ectodermal layer than in those derived form endodermal or mesodermal layers. These results suggest that the MPS-1 sequence may be a ubiquitous marker for ectodermally derived malignancies.

EXAMPLE 15

Testing of Cultured Cell Lines for the Presence of MPS-1 mRNA

Several cultured human cell lines were examined by Northern blot analyses for the presence of the MPS-1 0.35-kb mRNA, using the $^{32}$P-labelled 250 bp DNA probe prepared as described above. Two melanoma cell lines (RPMI-7951 and SK-MEL-28) had the highest levels of expression of all cultured cell lines studied. MPS-1 was expressed at high level in three human breast carcinoma cell lines (MDA-MB-468, BT-20, and MDA-MB-231). MPS-1 was present at intermediate levels in neural cancers (LAN-5 neuroblastoma; U-138-MG glioblastoma), vulvar carcinoma (A-431), tongue carcinoma (SCC-15), lung carcinoma (A-549), and prostatic carcinoma (DU-145 and PC-3) cell lines. In contrast, cultured normal WI-38 human lung fibroblasts showed the lowest levels of MPS-1 mRNA expression. In general, these analyses revealed 3- to 10-fold higher MPS-1 mRNA expression in cancerous cells than in normal WI-38 cells.

BIBLIOGRAPHY

1. Fernandez-Pol, J. A., et. al., Proc. Natl. Acad. Sci., U.S.A., 74: 2889–2893, 1977.

2. Fernandez-Pol, J. A., J. Supramol. Struc., 11: 371–390, 1979.

3. Fernandez-Pol, J. A., FEBS Letters, 143: 86–92, 1982.

4. Fernandez-Pol, J. A., J. Cellular Biochem, 19: 205–222, 1982.

5. Fernandez-Pol, J. A., J. Biol. Chem., 260: 5003–5011, 1985.

6. Fernandez-Pol, J. A., et. al., Cancer Research, 46: 5153–5161, 1986

7. Fernandez-Pol, J. A., el. at., Cancer Research, 47: 4260–4265, 1987.

8. Fernandez-Pol, J. A., In Cancer and Aging, Progress in Research and Treatment, T. V. Zenser and R. M. Coe, Eds., Springer Publishing Co., New York, 1989, pp. 171–183.

9. Fernandez-Pol, J. A., et. al., J. Biol. Chem., 264: 4151–4156, 1989.

10. Fernandez-Pol, J. A., et. al., J. Cellular Biochem., 41: 159–170, 1989.

11. Fernandez-Pol, J. A., Modulation of EGF Receptor Protooncogene Expression by Growth Factors and Hormones in Human Breast Carcinoma cells. Critical Reviews in Oncogenesis. Eds. E. Pimentel and M. Perucho, CRC press, Boca Raton, Fla., 2: 173–185, 1991.

12. Fernandez-Pol, J. A., Growth Factors, Oncogenes, Antioncogenes and Aging, In Geriatric Oncology, L. Balducci (Ed.), J. B. Lippincott Co., Philadelphia, In press, 1991.

13. Sporn, et. al., J. Cell Biology, 105: 1039–1045, 1987.

14. Schultz, G. S. et. al., Science 235: 350–352, 1987.

15. Burk K. B. et al. Oncogenes. Springer-Verlag, New York, 1988.

16. Cooper, G. M. Oncogenes. Jones and Bartlett Publishers, Boston., 1990.

17. Seshadri, T. and Campisi, J. Science 247: 205–209, 1990.

18. Luckow, V. A., and Summers, M.D., Bio/technology, 6: 47–55, 1988.

19. Ensoli, B., et. al., Nature, 345: 84–86, 1990.

20. Frankel, A. D., and Pabo, C. O., Cell, 55: 1189–1193, 1988.

21. Kyte, J., and Doolittle, R. F., J. Mol. Biol., 157: 105–132, 1982.

22. Morishita, K., et. al., Cell, 54: 831–840, 1988.

23. Christy, B. A., et. al., Proc. Natl. Acad. Sci. U.S.A., 85: 7857–7861, 1988.

24. Bravo, R., Cell Growth and Differentiation, 1: 305–309, 1990.

25. Evans, R. M., and Hollenberg, S. M., Cell, 52: 1–3, 1988.

26. Berg, J. M., J. Biol. Chem., 265: 6513–6516, 1990.

27. Brown et. al., FEBS letters 186: 271–274, 1985.

28. Berg, J. M., In Progress in Inorganic chemistry, 37: 143–190, 1989.

29. Wright, J. J., et. al., Science, 248: 588–591, 1990.

30. Kozak, M., Nucleic Acid Research, 15: 8125–8148, 1987.

31. Lipman, D. J. and Pearson, W. R., Science, 227: 1435–1441, 1985.

32. Larson et. al., J. Nucl. Med., 24: 123–128, 1983.

33. Sternberger, Immunocytochemistry, John Wiley and Sons, New York, 1979.

34. Garrigues et. al., Int. J. Cancer 29: 511–515, 1982.

35. Southern, E. M., J. Mol. Biol. 98, 503–510, 1975.

36. Brenner, C. A., et. al., BioTechniques, 7: 1096–1103, 1989.

37. Erlich, H. A. (Ed.), PCR Technology, M Stockton press, New York, 1989.

38. Innis, M. A. et al (Eds) PCR Protocols. Academic Press, San Diego, 1990.

39. Dolle, P. et. al. Nature 342: 702–705, 1989.

40. Niedobitek, G. et al., Path. Res. Pract. 184: 343–348, 1989.

41. Lum, J. B. BioTechniques 4: 32–39, 1986.

42. Bresser, J. and Evinger-Hodges, M. J. Gene Anal Tech 4: 89–104, 1987.

43. Smith, G., In Methods in Enzymology, 151: 530–539, 1987.

44. Maggio, E. T. (Ed.) Enzyme-immunoassay. CRC Press, Inc., Boca Raton, Fla., 1980.

45. Langan, J. and Clapp, J. J. Ligand Assay. Masson Publishing U.S.A., Inc. New York, 1981.

46. Lefkovits, I and Pernis, B. (Eds) Immunological Methods I and IX. Academic Press, New York, 1981.

47. Kohler, G. and Milstein, C., Nature(London) 256:695–699, 1975.

48. Sanger, F., et al., Proc. Natl. Acad. Sci. USA, 74:5463–5467, 1977.

49. Jansen, R., and Ledley, F. D., Gene Anal. Techn., 6:79–83, 1989.

50. Ollo, R., and Maniatis, T., Proc. Natl. Acad. Sci. USA, 84:5700–5740, 1987.

51. Means, G. E. and Feeney, R. E. "Chemical Modification of Proteins", pp 1–230, Holden-Day, San Francisco, 1971.

52. Watson, J. D., et al. "Molecular Biology of the Gene", pp 730–735, The Benjamin/Cummings Publishing Co., Menlo Park, Calif., 1988.

53. Kalderon, D., et al., Cell, 39:499–509, 1984.

54. Silver, P. A. et al, Proc. Natl. Acad. Sci. USA, 81:5951–5955,1984.

55. Siegall, C. B., et. al., FASEB J. 3:2647–2652, 1989.

56. Lorberboum-Galski, H., et al., Proc. Natl. Acad. Sci. USA, 85:1922–1926, 1988.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 329 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Human female carcinoma tumor cells
( C ) INDIVIDUAL ISOLATE: ST1H2
( F ) TISSUE TYPE: Carcinoma
( G ) CELL TYPE: Human
( H ) CELL LINE: MDA-468

( v i i ) IMMEDIATE SOURCE:
( B ) CLONE: ST1H2

( i x ) FEATURE:
( A ) NAME/KEY: CDS
( B ) LOCATION: 21..275
( C ) IDENTIFICATION METHOD: experimental
( D ) OTHER INFORMATION: /function="Zinc finger protein, transcription activation"
/ product="Metallopanstimulin-1"
/ evidence=EXPERIMENTAL
/ standard_name="MPS-1"

( x i ) SEQUENCE DESCRIPTION: SEQ ID NO:1:

```
CGACCTACGC ACACGAGAAC ATG CCT CTC GCA AAG GAT CTC CTT CAT CCC      50

                          Met Pro Leu Ala Lys Asp Leu Leu His Pro
                           1               5                  10

TCT CCA GAA GAG GAG AAG AGG AAA CAC AAG AAG AAA CGC CTG GTG CAG    98
Ser Pro Glu Glu Glu Lys Arg Lys His Lys Lys Lys Arg Leu Val Gln
                15                  20                  25

AGC CCC AAT TCC TAC TTC ATG GAT GTG AAA TGC CCA GGA TGC TAT AAA   146
Ser Pro Asn Ser Tyr Phe Met Asp Val Lys Cys Pro Gly Cys Tyr Lys
            30                  35                  40

ATC ACC ACG GTC TTT AGC CAT GCA CAA ACG GTA GTT TTG TGT GTT GGC   194
Ile Thr Thr Val Phe Ser His Ala Gln Thr Val Val Leu Cys Val Gly
        45                  50                  55

TGC TCC ACT GTC CTC TGC CAG CCT ACA GGA GGA AAA GCA AGG CTT ACA   242
Cys Ser Thr Val Leu Cys Gln Pro Thr Gly Gly Lys Ala Arg Leu Thr
    60                  65                  70

GAA GGA TGT TCC TTC AGG AGG AAG CAG CAC TAAAAGCACT CTGAGTCAAG     292
Glu Gly Cys Ser Phe Arg Arg Lys Gln His
75                  80                  85

ATGAGTGGGA AACCATCTCA ACAAACACAT TTTGGAT                          329
```

( 2 ) INFORMATION FOR SEQ ID NO:2:

( i ) SEQUENCE CHARACTERISTICS:
( A ) LENGTH: 84 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Pro Leu Ala Lys Asp Leu Leu His Pro Ser Pro Glu Glu Glu Lys
1               5                   10                  15

Arg Lys His Lys Lys Lys Arg Leu Val Gln Ser Pro Asn Ser Tyr Phe
            20                  25                  30

Met Asp Val Lys Cys Pro Gly Cys Tyr Lys Ile Thr Thr Val Phe Ser
        35                  40                  45

His Ala Gln Thr Val Val Leu Cys Val Gly Cys Ser Thr Val Leu Cys
    50                  55                  60

Gln Pro Thr Gly Gly Lys Ala Arg Leu Thr Glu Gly Cys Ser Phe Arg
65                  70                  75                  80

Arg Lys Gln His
```

I claim:

1. An isolated nucleic acid molecule which encodes a protein, designated metallopanstimulin-1, which has the amino acid sequence shown in FIG. 4 (SEQ ID NO:2).

2. A genetic vector which replicates in E. coli comprising the nucleic acid molecule of claim 1.

3. A genetic vector capable of transfecting insect cells comprising the nucleic acid molecule of claim 1.

4. Transformed bacterial cells comprising the vector of claim 2.

5. Transfected insect cells comprising the vector of claim 3.

6. An isolated nucleic acid probe consisting of nucleotides 21–41 of SEQ ID NO:1 or nucleotides complementary to nucleotides 236–256 of SEQ ID NO:1.

7. The isolated nucleic acid probe of claim 6 which is conjugated to at least one biotin moiety.

8. The isolated nucleic acid probe of claim 6 which is conjugated to at least one fluorescent moiety.

9. The isolated nucleic acid probe of claim 6 which is radioactively labeled.

*10. An isolated nucleic acid molecule which encodes a mutein of metallopanstimulin-1 having the amino acid sequence shown in FIG. 4 (SEQ ID NO:2), wherein one or both cysteine residues at positions 64 and 77 have been replaced by another amino acid.*

*11. A recombinant expression vector comprising the nucleic acid molecule of claim 1 or claim 10.*

*12. A host cell transformed or transfected with an expression vector of claim 11.*

*13. A process for preparing metallopanstimulin-1 polypeptide comprising culturing a host cell according to claim 12 under conditions promoting expression, and recovering metallopanstimulin-1 polypeptide from the culture.*

*14. The vector of claim 11 comprising a chimeric gene wherein the nucleic acid which encodes metallopanstimulin-1 or mutein thereof is operatively linked to a nucleic acid which encodes a heterologous polypeptide.*

*15. A host cell transformed or transfected with an expression vector of claim 14.*

*16. A process for preparing a metallopanstimulin-1 polypeptide or mutein thereof comprising culturing a host cell according to claim 15 under conditions promoting expression, and recovering the metallopanstimulin-1 polypeptide or mutein thereof from the culture.*

*17. A probe comprising nucleotides 21-256 of SEQ ID NO:1.*

*18. The probe of claim 17 which is conjugated to at least one biotin unit.*

*19. The probe of claim 17 which in conjugated to at least one one fluorescent unit.*

*20. The probe of claim 17 which is radioactively labeled.*

* * * * *

UNITED STATES PATENT AND TRADEMARK OFFICE

CERTIFICATE OF CORRECTION

PATENT NO. : Re. 35,585
DATED : August 12, 1997
INVENTOR(S) : Jose A. Fernandez-Pol It is certified that error appears in the above-indentified patent and that said Letters Patent is hereby corrected as shown below:

Column 42, Line 22
delete --in--
add -- is--

Column 42, Line 23
delete one of the word -- one--

Signed and Sealed this

Second Day of December,1997

*Attest:*

*Attesting Officer*

BRUCE LEHMAN

*Commissioner of Patents and Trademarks*